US009603554B2

(12) United States Patent
Liang et al.

(10) Patent No.: US 9,603,554 B2
(45) Date of Patent: Mar. 28, 2017

(54) SYSTEMS, METHODS, AND MEDIA FOR MONITORING THE CONDITION OF A PATIENT'S HEART

(71) Applicants: Arizona Board of Regents, for and on Behalf of, Arizona State University, Scottsdale, AZ (US); Mayo Foundation for Medical Education and Research, Rochester, MN (US)

(72) Inventors: Jianming Liang, Phoenix, AZ (US); Nima Tajbakhsh, Phoenix, AZ (US); Wenzhe Xue, Chandler, AZ (US); Hong Wu, Tempe, AZ (US); Eileen McMahon, Scottsdale, AZ (US); Marek Belohlavek, Scottsdale, AZ (US)

(73) Assignees: The Arizona Board of Regents, Scottsdale, AZ (US), on behalf of Arizona State University; Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/376,568

(22) PCT Filed: Feb. 4, 2013

(86) PCT No.: PCT/US2013/024677
§ 371 (c)(1),
(2) Date: Aug. 4, 2014

(87) PCT Pub. No.: WO2013/116867
PCT Pub. Date: Aug. 8, 2013

(65) Prior Publication Data
US 2015/0099990 A1    Apr. 9, 2015

Related U.S. Application Data

(60) Provisional application No. 61/594,984, filed on Feb. 3, 2012.

(51) Int. Cl.
*A61B 5/11* (2006.01)
*A61B 5/02* (2006.01)
(Continued)

(52) U.S. Cl.
CPC ........ *A61B 5/1102* (2013.01); *A61B 5/02007* (2013.01); *A61B 5/02028* (2013.01);
(Continued)

(58) Field of Classification Search
None
See application file for complete search history.

(56) References Cited

U.S. PATENT DOCUMENTS 7,526,101 B2    4/2009  Avidan
7,840,061 B2    11/2010 Porikli et al.
(Continued)

OTHER PUBLICATIONS

"Deep Vein Thrombosis Overview", Technical Report, Society of Interventional Radiology, last accessed Sep. 17, 2014, pp. 1-3, available at: http://www.sirweb.org/patients/deep-vein-thrombosis/.
(Continued)

*Primary Examiner* — Brian T Gedeon
*Assistant Examiner* — Ankit D Tejani
(74) *Attorney, Agent, or Firm* — Byrne Poh LLP

(57) ABSTRACT

Receiving a plurality of images of a first wall of the patient's heart, the plurality including a first image captured at a time ij and a second image captured at a time $t_2$, determining, based on the plurality of images, a first characteristic of movement of at least a wall portion of the first wall during a time period spanning time $t_1$ and time $t_2$, the first characteristic of movement being determined by using one or more image processing techniques, and the first, characteristic of movement being based on at least one of: (i) a shape of the wall portion in the first image and a shape of the wall portion in the second image, and (ii) a location of the wall portion
(Continued)

in the first image and a location of the wall portion in the second image: and outputting an indication of the first characteristic of movement.

9 Claims, 17 Drawing Sheets

(51) Int. Cl.
*G06T 7/00* (2017.01)
*G06T 7/20* (2017.01)
*A61B 8/08* (2006.01)
*A61B 5/00* (2006.01)
*A61B 8/06* (2006.01)

(52) U.S. Cl.
CPC .......... *A61B 5/7282* (2013.01); *A61B 8/0883* (2013.01); *G06T 7/0016* (2013.01); *G06T 7/2033* (2013.01); *A61B 8/065* (2013.01); *A61B 2576/023* (2013.01); *G06T 2207/10016* (2013.01); *G06T 2207/10132* (2013.01); *G06T 2207/20076* (2013.01); *G06T 2207/20224* (2013.01); *G06T 2207/30048* (2013.01); *G06T 2207/30241* (2013.01)

(56) References Cited

U.S. PATENT DOCUMENTS

| | | | |
|---|---|---|---|
| 8,812,431 B2 | 8/2014 | Voigt et al. | |
| 2003/0199762 A1 | 10/2003 | Fritz et al. | |
| 2004/0208341 A1* | 10/2004 | Zhou | G06K 9/3216 382/103 |
| 2005/0220336 A1 | 10/2005 | Sabe et al. | |
| 2005/0228276 A1 | 10/2005 | He et al. | |
| 2006/0074834 A1 | 4/2006 | Dong et al. | |
| 2006/0204121 A1 | 9/2006 | Bryll | |
| 2007/0280530 A1 | 12/2007 | Fung et al. | |
| 2008/0009733 A1 | 1/2008 | Saksena | |
| 2008/0027887 A1 | 1/2008 | Barbu et al. | |
| 2008/0089571 A1* | 4/2008 | Kurita | A61B 8/08 382/131 |
| 2008/0154565 A1 | 6/2008 | Florin et al. | |
| 2008/0171939 A1 | 7/2008 | Ishihara | |
| 2008/0192887 A1 | 8/2008 | Weese et al. | |
| 2008/0194957 A1* | 8/2008 | Hoctor | A61B 8/483 600/443 |
| 2008/0205750 A1 | 8/2008 | Porikli et al. | |
| 2008/0240532 A1 | 10/2008 | Carneiro et al. | |
| 2008/0260230 A1 | 10/2008 | Gotardo et al. | |
| 2009/0034816 A1 | 2/2009 | Ghanem et al. | |
| 2009/0060307 A1 | 3/2009 | Ghanem et al. | |
| 2009/0175515 A1 | 7/2009 | Schummers | |
| 2009/0252394 A1 | 10/2009 | Liang et al. | |
| 2010/0046815 A1 | 2/2010 | Von Berg et al. | |
| 2010/0061601 A1 | 3/2010 | Abramoff et al. | |
| 2010/0076517 A1* | 3/2010 | Imran | A61N 1/362 607/35 |
| 2010/0098308 A1 | 4/2010 | Lakare et al. | |
| 2010/0113930 A1 | 5/2010 | Miyachi | |
| 2010/0177944 A1 | 7/2010 | Madabhushi et al. | |
| 2010/0202681 A1 | 8/2010 | Ai et al. | |
| 2010/0266176 A1* | 10/2010 | Masumoto | G06F 19/321 382/128 |
| 2011/0191283 A1 | 8/2011 | Voigt et al. | |
| 2011/0270089 A1 | 11/2011 | Vezina | |
| 2011/0293157 A1 | 12/2011 | Ye et al. | |
| 2012/0089545 A1 | 4/2012 | Mei et al. | |
| 2012/0106815 A1 | 5/2012 | Yang et al. | |
| 2012/0274755 A1 | 11/2012 | Sinha et al. | |
| 2013/0070997 A1 | 3/2013 | Tajbakhsh et al. | |
| 2014/0185887 A1 | 7/2014 | Wu et al. | |

OTHER PUBLICATIONS

Alonso-Martnez, J.L., et al., "Delay and misdiagnosis in submassive and non-massive acute pulmonary embolism", In European Journal of Internal Medicine, vol. 21, No. 4, Aug. 2010, pp. 278-282.

Araoz, P.A., et al., "Helical ct pulmonary angiography predictors of in-hospital morbidity and mortality in patients with acute pulmonary embolism", In Journal of Thoracic Imaging, vol. 18, Oct. 2003, pp. 207-216.

Bi, J. and Liang, J., "Multiple instance learning of pulmonary embolism detection with geodesic distance along vascular structure", In Proceedings of IEEE Computer Society Conference on Computer Vision and Pattern Recognition (CVPR) Jun. 17-22, 2007, Minneapolis, MN, USA, pp. 1-8.

Bottiger, B.W., et al., "Inhaled nitric oxide selectively decreases pulmonary artery pressure and pulmonary vascular resistance following acute massive pulmonary microembolism in piglets," In Chest, vol. 110, No. 4, Oct. 1996, pp. 1041-1047.

Bouma, H., "Vessel-Diameter Quantification and Embolus Detection in CTA Images." Ph.D. Thesis, Eindhoven University of Technology, PrintPartners, Ipskamp, The Netherlands, Apr. 2008, pp. 9-133.

Bouma, H., et al, "Automatic Detection of Pulmonary Embolism in CTA Images", In IEEE Transactions on Medical Imaging, vol. 28, No. 8, Aug. 2009, pp. 1223-1230.

Bourdev, L. and Brandt, J., et al., "Robust Object Detection Via Soft Cascade", In Proceedings of the 2005 IEEE Conference on Computer Vision and Pattern Recognition (CVPR '05), Washington, DC, USA, Jun. 2005, pp. 236-243.

Chartrand-Lefebvre, C., "Computed tomography angiography in the diagnosis of pulmonary embolism: Interobserver agreement", In American Journal of Emergency Medicine, Jan. 27, 2011, pp. 118-119.

Cho, E.J., et al., "Right ventricular free wall circumferential strain reflects graded elevation in acute right ventricular afterload", In Am J Physiol Heart Circ Physiol., Feb. 2009, vol. 296, No. 2, pp. 818-824.

Collomb, J., et al., "Severity Assessment of Acute Pulmonary Embolism: Evaluation using Helical CT," In European Radiology, vol. 13, No. 7, 2003, pp. 1508-1514.

Costantino, G., et al., "Interobserver agreement in computer tomography readings for pulmonary embolism", In American Journal of Emergency Medicine, Jan. 27, 2011, pp. 119.

Costantino, G., et al., "Interobserver agreement in computer tomography readings for pulmonary embolism", In American Journal of Emergency Medicine, vol. 27, No. 9, Nov. 2009, pp. 1109-1111.

Craig, J.J., "Introduction to Robotics: Mechanics and Control", 3rd edition, Prentice Hall, Aug. 6, 2004, pp. 1-385.

Criminisi, A., et al., "Regression Forests for Efficient Anatomy Detection and Localization in CT Studies", In Proceedings of the International Workshop on Medical Computer Vision, Beijing, CN, Sep. 2010, pp. 106-117.

Crow, F.C., "Summed-Area Tables for Texture Mapping", In Computer Graphics, vol. 18, no, Jul. 3, 1984, pp. 207-212.

Dias-Junior, C.A., "The effect of sildenafil on pulmonary embolism-induced oxidative stress and pulmonary hypertension", In Anesthesia & Analgesia, vol. 101, No. 1, Jul. 2005, pp. 115-120.

Dinesh, M.S., et al, "Adaptive Contrast-Based Computer Aided Detection for Pulmonary Embolism", In Proceedings of the SPIE International Society Conference for Optimal Engineering, Mar. 2009, vol. 7260, No. 726010, pp. 1-8.

Dollar, P., et al., "Multiple Component Learning for Object Detection", In Proceedings of the 10th European Conference on Computer Vision: Part II (ECCV '08), Marseille, FR, Oct. 12-18, 2008, pp. 211-224.

Dousset, M., et al., "Principles and performance of virtual CT and MIRA intraluminal endoscopy", In Virtual Endoscopy, Springer, Nov. 2002, pp. 1-19.

(56) References Cited

OTHER PUBLICATIONS

Frangi, A.F., et al., "Multiscale vessel enhancement filtering", In Medical Image Computing and Computer-Assisted Intervention, Oct. 11-13, 1998, pp. 130-137.
Freund, Y. and Schapire, R.E., "A Decision-Theoretic Generalization of On-Line Learning and an Application to Boosting", In Journal of Computer and System Sciences, vol. 55, No. 1, Aug. 1997, pp. 119-139.
Freund, Y. and Schapire, R.E., "A Short Introduction to Boosting", In Journal of Japanese Society for Artificial Intelligence, vol. 14, No. 5, Sep. 1999, pp. 771-780.
Galson, S.K., "The surgeon general's call to action to prevent deep vein thrombosis and pulmonary embolism", Technical Report, U.S. Public Health Services, Sep. 15, 2008, pp. 1-35.
Ghaye, B., et al., "Can CT Pulmonary Angiography Allow Assessment of Severity and Prognosis in Patients Presenting with Pulmonary Embolism? What the Radiologist Needs to Know," In RadioGraphics, vol. 26, Jan. 2006, pp. 23-29.
Ghaye, B., et al., "Severe pulmonary embolism: pulmonary artery clot load scores and cardiovascular parameters as predictors of mortality," In Radiology, vol. 239, 2006, pp. 884-891.
Godec, M., et al., "On-line Random Naive Bayes for Tracking", In Proceedings of the 20th International Conference (ICPR '10), Istanbul, TR, Aug. 23-26, 2010, pp. 3545-3548.
Goldstein, H., "Classical Mechanics", 2nd Edition, Jul. 1980, pp. 1-2.
Grabner, H. and Bischof, H., "On-line Boosting and Vision", In Proceedings of the IEEE Computer Society Conference on Computer Vision and Pattern Recognition (CVPR '06), New York, NY, USA, Jun. 17-22, 2006, pp. 260-267.
Grbovic, M. and Vucetic, S., "Tracking Concept Change with Incremental Boosting by Minimization of the Evolving Exponential Loss", In Proceedings of the European Conference on Machine Learning and Knowledge Discovery in Databases, Athens, GR, Sep. 5-9, 2011, pp. 516-532.
Grifoni, S.,"Short-term clinical outcome of patients with acute pulmonary embolism, normal blood pressure, and echocardiographic right ventricular dysfunction," In Circulation, vol. 101, No. 24, Jun. 2000, pp. 2817-2822.
Groth, M., et al., "Correlation of right ventricular dysfunction parameters and pulmonary vascular obstruction score in acute pulmonary embolism in a porcine model", In Emergency Radiology, Sep. 2010, pp. 367-374.
He, H., et al., "Incremental Learning from Stream Data," In IEEE Transactions on Neural Networks, vol. 22, No. 12, Dec. 2011, pp. 1901-1914.
International Patent Application No. PCT/US2013/024675, filed Feb. 4, 2013.
International Preliminary Report on Patentability dated Aug. 22, 2013 in International Patent Application No. PCT/US2012/024925.
International Preliminary Report on Patentability in International Application No. PCT/US2012/024907, filed Feb. 13, 2012, mailed Aug. 22, 2013.
International Search Report in International Patent Application No. PCT/US2012/024925, filed Feb. 13, 2012, mailed Jun. 19, 2012.
International Search Report in International Patent Application No. PCT/US2013/024675, filed Feb. 4, 2013, mailed Apr. 16, 2013.
International Search Report in International Patent Application No. PCT/US2013/024677, filed Feb. 4, 2013, mailed Apr. 15, 2013.
Jardin, F., et al., "Echocardiographic pattern of acute cor pulmonale," In Chest, vol. 111, No. 1, Jan. 1997, pp. 209-217.
Kanitsar, A., et al., "CPR—Curved Planar Reformation", In Proceedings of IEEE Visualization, Nov. 1, 2002, pp. 37-44.
Kass, M., et al., "Snakes: Active contour models," In International Journal of Computer Vision, vol. 1, No. 4, Jan. 1988, pp. 321-331.
Kim, T.K., et al., "Online Multiple Classier Boosting for Object Tracking", In Proceedings of the 2010 IEEE Computer Society Conference on Computer vision and Pattern Recognition Workshops (CVPRW '10), San Francisco, CA, USA, Jun. 13-18, 2010, pp. 1-6.
Kiraly, A.P., et al., "Cartwheel projections of segmented pulmonary vasculature for the detection of pulmonary embolism", In Medical Imaging: Visualization, Image-Guided Procedures, and Display, Proc. SPIE 5744, Apr. 12, 2005, pp. 69-78.
Knutsson, H., "Representing Local Structure using Tensors", In Proceedings of the 6th Scandinavian Conference on Image Analysis, Oulu, Finland, Jun. 1989, pp. 244-251.
Kothe, U., "Edge and Junction Detection with an Improved Structure Tensor", In Proceedings of the 25th DAGM Symposium on Pattern Recognition, Magdeburg, DE, Sep. 10-12, 2003, pp. 25-32.
Kurkure, U., et al., "Automated Segmentation of Thoracic Aorta in Non-Contrast CT Images", In Proceedings of the 5th International Symposium on Biomedical Imaging: From Nano to Macro (ISBI '08), Paris, FR, May 14-17, 2008, pp. 29-32.
Leistner, C., et al., "On Robustness of On-Line Boosting—A Competitive Study", In Proceedings of the 2009 IEEE 12th International Conference on Computer Vision Workshops (ICCVW '09), Kyoto, JP, Sep. 27-Oct. 4, 2009, pp. 1362-1369.
Levenberg, K., "A method for the solution of certain non-linear problems in least squares", In Quarterly Journal of Applied Mathmatics, vol. 2, 1944, pp. 164-168.
Liang, J. and Bi, J., "Computer Aided Detection of Pulmonary Embolism with Tobogganing and Multiple Instance Classification in CT Pulmonary Angiography", In Proceedings of the 20th Intl Conference of Information Processing in Medical Imaging Kerkrade, NL, Jul. 2-6, 2007, pp. 630-641.
Liang, J. and Bi, J., "Local Characteristic Features for Computer-Aided Detection of Pulmonary Embolism in CT Angiography", In Proceedings of the First Workshop on Pulmonary Image Analysis, New York, NY, US, Sep. 6, 2008, pp. 263-272.
Liang, J., et al., "United Snakes", In Medical Image Analysis, vol. 10 No. 2, Apr. 2006, vol. 215-233.
Liu, D., et al., "Search strategies for multiple landmark detection by submodular maximization", IEEE Conference on Computer Vision and Pattern Recognition, Jun. 3-8, 2010, San Francisco, CA, USA, pp. 2831-2838.
Liu, X. and Yu, T., "Gradient Feature Selection for Online Boosting", In Proceedings of the IEEE 11th International Conference on Computer Vision (ICCV '07), Rio de Janeiro, BR, Oct. 14-21, 2007, pp. 1-8.
Lorenz, C., et al., "Multi-scale line segmentation with automatic estimation of width, contrast and tangential direction in 2-D and 3-D medical images", In Proceedings of the 1st Joint Conference on Computer Vision, Virtual Reality and Robotics in Medicine and Medical Robotics, London, UK, Mar. 19-22, 1997, pp. 233-242.
Mansencal, N., "Comparison of different echocardiographic indexes secondary to right ventricular obstruction in acute pulmonary embolism," In the American Journal of Cardiology, vol. 92, No. 1, Jul. 2003, pp. 116-119.
Marquardt, D.W., "An Algorithm for Least-Squares Estimation of Nonlinear Parameters," In SIAM Journal on Applied Mathematics, vol. 11 No. 2, Jun. 1963, pp. 431-441.
Mastora, I., "Severity of acute pulmonary embolism: evaluation of a new spiral ct angiographic score in correlation with echocardiographic data", In European Radiology, vol. 13, Jan. 2003, pp. 29-35.
Masutani, Y., et al., "Computerized Detection of Pulmonary Embolism in Spiral CT Angiography Based on Volumetric Image Analysis", In IEEE Transactions on Medical Imaging, vol. 21, No. 12, Dec. 2002, pp. 1517-1523.
McConnell, M.V., et al., "Regional right ventricular dysfunction detected by echocardiography in acute pulmonary embolism," In the American Journal of Cardiology, vol. 78 No. 4, Aug. 1996, pp. 469-473.
Office Action dated Jul. 17, 2014 in U.S. Appl. No. 13/621,837.
Office Action dated Aug. 16, 2013 in U.S. Appl. No. 13/984,800.
Office Action dated Aug. 23, 2013 in U.S. Appl. No. 13/984,808.
Office Action dated Sep. 18, 2013 in U.S. Appl. No. 12/744,949.4.
Office Action dated Oct. 7, 2013 in U.S. Appl. No. 14/023,380.
Office Action dated Sep. 18, 2013 in European Patent Application No. 12744949.4.

(56) References Cited

OTHER PUBLICATIONS

Ouellette, D.R., et al., "Pulmonary Embolism", Medscape.com, last updated Sep. 4, 2014, available at: http://emedicine.medscape.com/article/300901-overview#showall, pp. 1-24.
Oza, N. C. and Russell, S., "Online Bagging and Boosting", In 8th International Workshop on Artificial Intelligence and Statistics, Key West, FL, USA, Jan. 2001, pp. 105-112.
Parag, T., et al., "Boosting Adaptive Linear Weak Classifiers for Online Learning and Tracking", In Proceedings of the IEEE Conference on Computer Vision and Recognition (CVPR '08), Anchorage, AK, USA, Jun. 23-28, 2008, pp. 1-8.
Parikh, D. and Polikar, R., "An Ensemble-Based Incremental Learning Approach to Data Fusion", In IEEE Transactions on Systems, Man, Cybernetics, Part B: Cybernetics, vol. 37, No. 2, Apr. 2007, pp. 437-450.
Pelossof, R., et al., "Online Coordinate Boosting", In Proceedings of the 2009 IEEE 12th International Conference on Computer Vision Workshops, (ICCVW '09), Kyoto, JP, Sep. 27-Oct. 4, 2009, pp. 1354-1361.
Pham, M. and Cham, T., "Detection with Multi-exit Asymmetric Boosting", In Proceedings of the IEEE Conference on Computer Vision and Pattern Recognition (CVPR '08), Anchorage, AK, USA, Jun. 23-28, 2008, pp. 1-8.
Pham, M. and Cham, T., "Fast Training and Selection of Haar Features Using Statistics in Boosting-Based Face Detection", In Proceedings of the IEEE 11th International Conference on Computer Vision (ICCV '07), Rio de Janeiro, BR, Oct. 14-21, 2007, pp. 1-7.
Pham, M. and Cham, T., "Online Learning Asymmetric Boosted Classifiers for Object Detection", In Proceedings of the IEEE Conference on Computer Vision and Recogition (CVPR '07), Minneapolis, MN, USA, Jun. 17-22, 2007, pp. 1-8.
Ribeiro, A., et al., "Echocardiography doppler in pulmonary embolism: Right ventricular dysfunction as a predictor of mortality rate," In American Heart Journal, vol. 134, No. 3, Mar. 1997, pp. 479-487.
Sato, Y. et al., "3-D multi-scale line filter for segmentation and visualization of curvilinear structures in medical images", In Proceedings of the 1st Joint Conference on Computer Vision, Virtual Reality and Robotics in Medicine and Medical Robotics and Computer-Assisted Surgery, London, UK, Mar. 19-22, 1997, pp. 213-222.
Schapire, R. E. and Singer, Y., "BoosTexter: A Boosting-Based System for Text Categorization", In Machine Learning, vol. 39, No. 2, May 1, 2000, pp. 135-168.
Schapire, R. E., "Theoretical Views of Boosting and Applications", In Algorithmic Learning Theory, Lecture Notes in Computer Science, vol. 1720, Dec. 1999, pp. 13-25.
Sebbe, R., "Computer-aided Diagnosis of Pulmonary Embolism in Opacified CT Images", Ph.D. Dissertation, Faculte Polytechnique de Mons, Universitaires de Louvain, Belgium, Feb. 20, 2007, pp. 1-124.
Simon, M., et al., "Paddle-wheel CT display of pulmonary arteries and other lung structures: a new imaging approach", In American Journal of Roentgenology, Jul. 2001, pp. 195-198.
Simon, M., et al., "Paddle-wheel multislice helical CT display of pulmonary vessels and other lung structures", In Radiologic Clinics of North America, May 2003, pp. 617-626.
Stein, P.D. and Hull, R.D., "Multidetector computed tomography for the diagnosis of acute pulmonary embolism", In Current Opinion Pulmonary Medicine, Sep. 2007, pp. 384-388.
Stein, P.D. and Matta, F., "Acute Pulmonary Embolism", In Current Problems in Cardiology, vol. 35, No. 7, Jul. 2010, pp. 314-376.
Sternig, S., et al., "Transient Boost: On-line Boosting with Transient Data", In Proceedings of the 2010 IEEE Computer Society Conference on Computer Vision and Pattern Recognition Workshops (CVPRW '10), San Francisco, CA, USA, Jun. 13-18, 2010, pp. 22-27.
Tajbakhsh, N., et al., "Motion analysis of right ventricular dysfunction under mild and moderate pressure overload caused by acute pulmonary embolism", In Ultrasound in Medicine and Biology, vol. 39, No. 11, Nov. 2013, pp. 2066-2074.
Tajbakhsh, N., et al., "Shape-based analysis of right ventricular dysfunction associated with acute pulmonary embolism", In SPIE Medical Imaging, vol. 8317, Mar. 2012, pp. 83170G-83170G.
Takamura, T., et al., "Reversible left ventricular regional non-uniformity quantified by speckle-tracking displacement and strain imaging in patients with acute pulmonary embolism," In Journal of the American Society of Echocardiography, vol. 24, No. 7, Apr. 2011, pp. 792-802.
Torbicki, A., et al., "Guidelines on the diagnosis and management of acute pulmonary embolism of the European Society of Cardiology", In Eur Heart J., vol. 29, No. 18, Sep. 2008, pp. 2276-2315.
Vaidehi, V., et al., "Multiclass Object Detection System in Imaging Sensor Network Using Haar-like Features and Joint-Boosting Algorithm", In Proceedings of the 2011 International Conference on Recent Trends in Information Technology (ICRTIT '11), Chennai, Tamil Nadu, IN, Jun. 3-5, 2011, pp. 1011-1015.
Viola, P. and Jones M., "Fast and Robust Classification Using Asymmetric AdaBoost and a Detector Cascade", In Proceedings of the Annual Conference on Neural Information Processing Systems, Vancouver, BC, CA, Dec. 3-8, 2001, pp. 1311-1318.
Viola, P. and Jones, M., "Rapid Object Detection using a Boosted Cascade of Simple Features", In Proceedings of the IEEE Computer Society Conference on Computer Vision and Pattern Recognition, Kauai, HI, USA. Dec. 8-14, 2001, pp. 511-518.
Written Opinion in International Patent Application No. PCT/US2012/024925, filed Feb. 13, 2012, mailed Jun. 19, 2012.
Written Opinion in International Patent Application No. PCT/US2013/024675, filed Feb. 4, 2013, mailed Apr. 16, 2013.
Written Opinion in International Patent Application No. PCT/US2013/024677, filed Feb. 4, 2013, mailed Apr. 15, 2013.
Wu, B. and Nevatia, R., "Improving Part Based Object Detection by Unsupervised, Online Boosting", In Proceedings of the IEEE Conference on Computer Vision and Pattern Recognition (CVPR '07), Minneapolis, MN, USA, Jun. 17-22, 2007, pp. 1-8.
Wu, H., et al. "Self-Adaptive Asymmetric On-line Boosting for Detecting Anatomical Structures", In SPIE Medical Imaging, vol. 8315, Feb. 2012, pp. 831539-831539.
Wu, H., et al., "Machine Learning based Automatic Detection of Pulmonary Trunk", In Proceedings of the SPIE Conference on Medical Imaging 2011: Computer-Aided Diagnosis, Lake Buena Vista, FL, USA, Feb. 12, 2011, vol. 7963, pp. 1-6.
Zheng, Y., et al., "Automatic Aorta Segmentation and Valve Landmark Detection in C-Arm CT: Application to Aortic Valve Implantation", In IEEE Transactions on Medical Imaging, vol. 31, No. 12, Dec. 2012, pp. 2307-2321.
Zheng, Y., et al., "Fast Automatic Heart Chamber Segmentation from 3D CT Data Using Marginal Space Learning and Steerable Features", In Proceedings of the IEEE 11th International Conference on Computer Vision (ICCV '07), Rio de Janeiro, BR, Oct. 14-21, 2007, pp. 1-8.
Zhou, C., et al., "Automatic Pulmonary Vessel Segmentation in 3D Computed Tomographic Pulmonary Angiographic (CTPA) Images", In Proceedings of the SPIE 6144, Medical Imaging: Image Processing, Mar. 15, 2006, pp. Q1-Q7.
Zhou, S. K., et al., "A Boosting Regression Approach to Medical Anatomy Detection", In Proceedings of the IEEE Conference on Computer Vision and Pattern Recognition (CVPR '07), Minneapolis, MN, USA, Jun. 17-22, 2007, pp. 1-8.
Zou, X., et al., "Anatomy-Based Automatic Detection and Segmentation of Major Vessels in Thoracic CTA Images", In Computerized Medical Imaging and Graphics, vol. 30, No. 5, Jul. 2006, pp. 299-313.
Frangi, A.F. et al., "Model-Based Quantitation of 3-D Magnetic Resonance Angiographic Images", In IEEE Transaction on Medical Imaging, vol. 18, No. 10, Oct. 1999, pp. 946-956.
Howard, G. et al., "Carotid Artery Intimal-Medial Thickness Distribution in General Populations as Evaluated by B-mode Ultrasound", In Stroke, vol. 24, No. 9, Sep. 1993, pp. 1297-1304.
Hurst, R. et al., "Clinical Use of Carotid Intima-Media Thickness: Review of the Literature", In Journal of the American Society of Echocardiography, vol. 20, No. 7, Jul. 2007, pp. 907-914.

(56) References Cited

OTHER PUBLICATIONS

Li, S. et al., "Childhood Cardiovascular Risk Factors and Carotid Vascular Changes in Adulthood: the Bogalusa Heart Study", In the Journal of the American Medical Association (JAMA), vol. 290, No. 17, Nov. 2003, pp. 2271-2276.
Notice of Allowance dated Sep. 14, 2015 in U.S. Appl. No. 13/621,837.
Office Action dated Jan. 4, 2016 in U.S. Appl. No. 14/023,380.
Office Action dated Jan. 22, 2015 in U.S. Appl. No. 14/376,181.
Office Action dated Jan. 29, 2015 in U.S. Appl. No. 13/621,837.
Office Action dated Jul. 20, 2016 in U.S. Appl. No. 13/984,808.
Office Action dated Sep. 21, 2015 in U.S. Appl. No. 13/984,808.
Patent Examination Report dated Aug. 26, 2015 in Australian Patent Application No. 2012241419.
Stein, J. et al., "A Semiautomated Ultrasound Border Detection Program that Facilitates Clinical Measurement of Ultrasound Carotid Intima-Media Thickness", In Journal of the American Society for Echocardiography, vol. 18, No. 3, Mar. 2005, pp. 244-251.
Stein, J. et al., "Use of Carotid Ultrasound to Identify Subclinical Vascular Disease and Evaluate Cardiovascular Disease Risk: A Consensus Statement from the American Society of Echocardiography Carotid Intima-Media Thickness Task Force", In Journ. Am. Soc. Echocardiography, vol. 21, No. 2, Apr. 2008, pp. 93-111.
Stein, J. et al., "Vascular Age: Integrating Carotid Intima-Media Thickness Measurements with Global Coronary Risk Assessment", In Clinical Cardiology, vol. 27, No. 7, Jul. 2004, pp. 388-392.
Wu, H., "Offline and Online Adaboost for Detecting Anatomical Structures", Thesis Paper, Arizona State University, Aug. 2011, pp. 1-66.

\* cited by examiner

SYSTEMS, METHODS, AND MEDIA FOR MONITORING THE CONDITION OF A PATIENT'S HEART

CROSS REFERENCE TO RELATED APPLICATION

This application claims the benefit of U.S. Provisional Patent Application No. 61/594,984, filed Feb. 3, 2012, which is hereby incorporated by reference herein in its entirety.

TECHNICAL FIELD

The disclosed subject matter relates to systems, methods, and media for monitoring the condition of a patient's heart.

BACKGROUND

Acute Pulmonary Embolism (APE) is known as one of the major causes of sudden death. APE is a blockage of the main artery of the lung or one of its branches by a substance that has traveled from elsewhere in the body through the bloodstream. For example, APE may result from a blood clot in the deep veins of the legs or pelvis braking off and migrating to the lung, a process termed venous thromboembolism (VTE). While massive APE produces diagnostically obvious symptoms of sudden severe hepoxia and right ventricle (RV) mechanical failure, little progress has been made in clinical and biophysical understanding of Acute Pulmonary Embolism in the early stages of its development. Such early detection can be of clinical importance in diagnosis and determination of prognosis of Acute Pulmonary Embolism.

SUMMARY

Systems, methods, and media for monitoring the condition of a patient's heart are provided. In accordance with some embodiments, systems for monitoring the condition of a patient's heart are provided. The systems include a hardware processor that is configured to: receive a plurality of images of a first wall of the patient's heart, the plurality including a first image captured at a time $t_1$ and a second image captured at a time $t_2$; determine, based on the plurality of images, a first characteristic of movement of at least a wall portion of the first wall during a time period spanning time $t_1$ and time $t_2$, the first characteristic of movement being determined by using one or more image processing techniques, and the first characteristic of movement being based on at least one of: (i) a shape of the wall portion in the first image and a shape of the wall portion in the second image, and (ii) a location of the wall portion in the first image and a location of the wall portion in the second image; and output an indication of the first characteristic of movement.

In accordance with some embodiments of the disclosed subject matter, methods for monitoring the condition of a patient's heart are provided. The methods comprising: receiving a plurality of images of a first wall of the patient's heart, the plurality including a first image captured at a time $t_1$ and a second image captured at a time $t_2$; determining, by a hardware processor, a first characteristic of movement of at least a wall portion of the first wall during a time period spanning time $t_1$ and time $t_2$, the first characteristic of movement being determined by using one or more image processing techniques, and the first characteristic of movement being based on at least one of: (i) a shape of the wall portion in the first image and a shape of the wall portion in the second image, and (ii) a location of the wall portion in the first image and a location of the wall portion in the second image; and outputting an indication of the first characteristic of movement.

In accordance with embodiments of the disclosed subject matter, non-transitory computer-readable media are provided that contain computer-executable instructions that, when executed by a hardware processor, cause the processor to perform a method for monitoring the condition of a patient's heart. In some embodiments, the method comprises: receiving a plurality of images of a first wall of a patient's heart, the plurality including a first image captured at a time $t_1$ and a second image captured at a time $t_2$; determining, based on the plurality of images, a first characteristic of movement of at least a wall portion of the first wall during a time period spanning time $t_1$ and time $t_2$, the first characteristic of movement being determined by using one or more image processing techniques, and the first characteristic of movement being based on at least one of: (i) a shape of the wall portion in the first image and a shape of the wall portion in the second image, and (ii) a location of the wall portion in the first image and a location of the wall portion in the second image; and outputting an indication of the first characteristic of movement.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION

When a patient experiences APE, the mechanical operation of the patient's right ventricle may change and the patient may experience a condition known as right ventricle (RV) overload. During RV overload, the right ventricle of a patient's heart may start to move irregularly, flatten, change shape, or begin to exhibit another type of abnormal behavior. Thus, by monitoring the condition of the patient's heart, RV overload may be detected.

In some embodiments of the disclosure, mechanisms (which may include systems, methods, non-transitory computer readable media, etc.) are provided for detecting RV overload. The mechanisms may obtain a plurality of images of a heart and use image processing techniques to determine the shape of the heart's septum in each image. The mechanisms may then compare the shape of the septum in one image to the shape of the septum in other images to determine how the septum's shape changes as the heart contracts and relaxes. If it is determined that the shape changes abnormally, the mechanisms may alert medical personnel to the abnormality, thereby providing medical personnel with an opportunity to detect APE in the early stages of its development.

In some embodiments of the disclosure, mechanisms are provided for detecting RV overload. The mechanisms may obtain a plurality of images of a heart and use image processing techniques to determine the location of the heart's septum in each image. The mechanisms may then use the information about the locations of the septum in first image, taken at time $t_1$, and a second image taken at time $t_2$, to determine a displacement of the septum during the period $t_1$-$t_2$. If it is determined that the septum has traveled an abnormal distance during that period, the mechanisms may alert medical personnel to the abnormality.

In some embodiments of the disclosure, mechanisms are provided for detecting RV overload. The mechanisms may obtain a plurality of images of a heart and use pattern recognition techniques to determine the location of the heart's septum in each image. The mechanisms may then determine the trajectory of movement of the septum during the heart's operation. If it is determined that the septum moves in an irregular fashion, the mechanisms may alert medical personnel to the irregularity.

Figure 1:
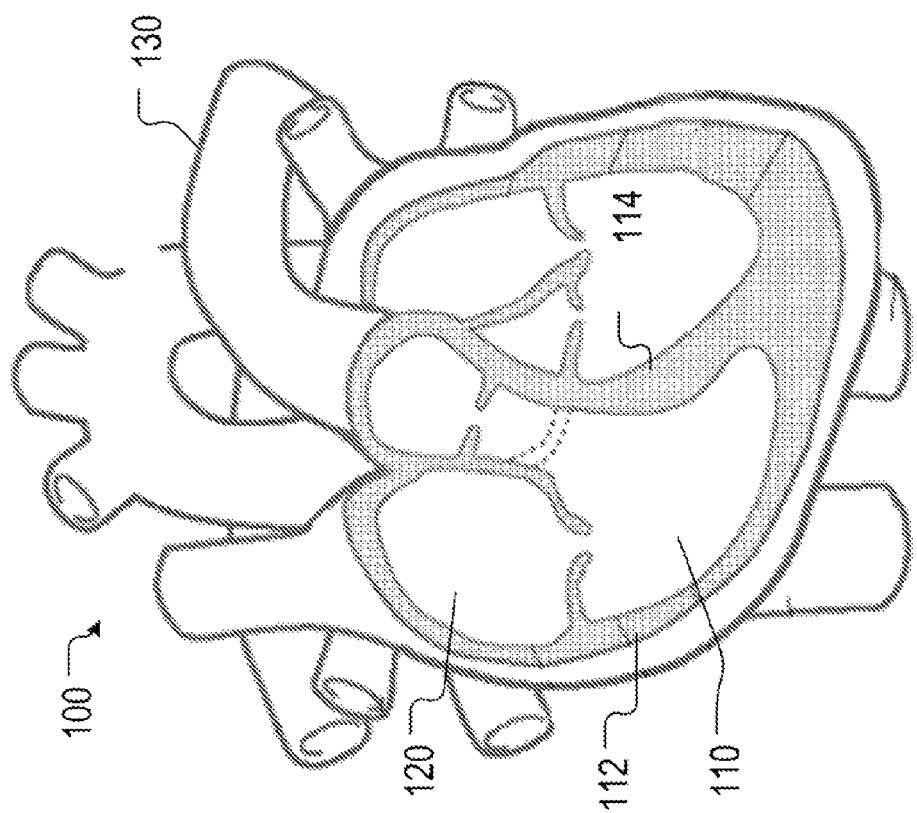
FIG. 1 is an example of a posterior cross-sectional view of a heart in accordance with some embodiments of the disclosed subject matter.

FIG. 1 is an example of a posterior cross-sectional view of a heart 100. As illustrated, the heart's right ventricle (RV) 110 is defined by a wall 112 and a wall 114. Wall 112 is the free boundary wall of RV 110 and wall 114 is the heart's septum. During the cardiac cycle, deoxygenated blood enters RV 110 from the heart's right atrium 120 and is subsequently ejected through the heart's pulmonary artery 130. When pulmonary artery 130 is clogged, the pressure in the pulmonary arterial system and the RV may increase, thereby resulting in RV overload which in turn could become fatal. As discussed above, during periods of RV overload, and prior to the condition becoming fatal, the biomechanics of heart 100 may change and become abnormal.

Figure 2:
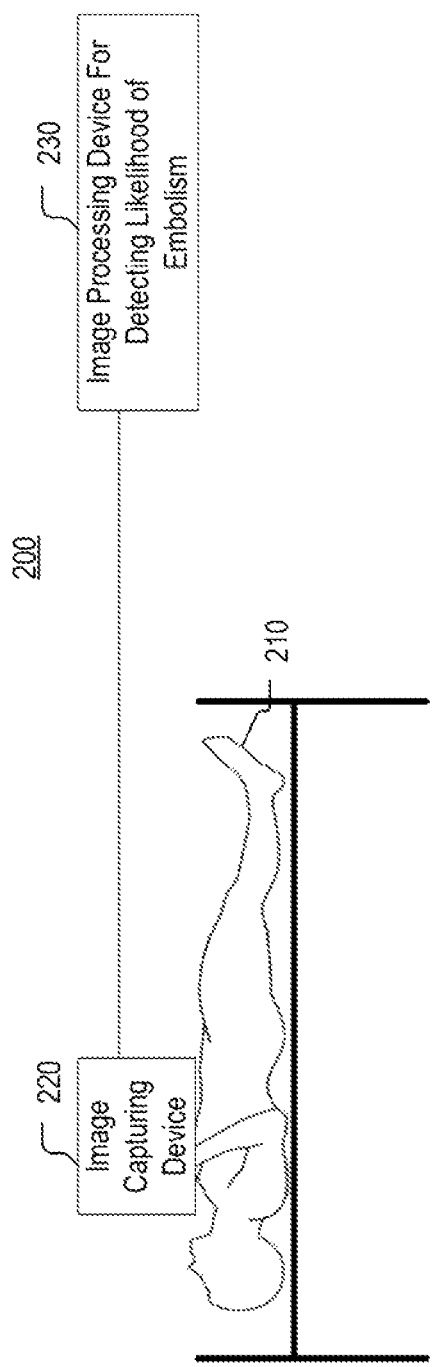
FIG. 2 is an example of a block diagram of an image processing system for cardiac monitoring in accordance with some embodiments of the disclosed subject matter.

FIG. 2 illustrates an example of a system 200 that performs analysis on cardiac images of a patient 210 to recognize abnormalities in the operation of heart 100 that occur during RV overload. As illustrated, system 200 may include an image capturing device 220 and an image processing device 230. Image capturing device 220 may include any suitable device for capturing images of heart 100 of patient 210, such as an ultrasound imaging device, an X-ray imaging device, a magnetic resonance imaging device, etc. Image processing device 230 may include any suitable device for processing images captured by image capturing device 220, such as a general purpose computer, a special purpose computer, a device that utilizes special-purpose circuitry (e.g., ASIC or FPGA) for the processing of images, etc. Image processing device 230 may be connected to image capturing device 220 via any suitable type of wired or wireless connection. The connection may be a network connection (e.g., LAN, WiFi, etc.) or another suitable type of connection, such as a USB connection or a serial interface connection. Furthermore, in some embodiments, image capturing device 220 and image processing device 230 may be integrated together into a single unit.

In operation, image processing device 230 may receive a plurality of images of heart 100 of patient 210. Image processing device 230 may then process the plurality of images to identify at least one characteristic of movement of at least one wall of the heart. Afterwards, image processing device 230 may output an indication of the characteristic for presentation to a user, such as a doctor or another type of medical personnel. In some embodiments, image processing device 230 may use the characteristic to estimate the likelihood of patient 210 having APE or the likelihood of patient 210 experiencing an RV overload.

As used herein, the term "image" may refer to multi-dimensional data composed of discrete image elements (e.g., pixels for two-dimensional images and voxels for three-dimensional images). The image may be, for example, a medical image of a subject collected using a computer tomography system, a magnetic resonance imaging system, an ultrasound imaging system, or any other medical imaging system or imaging modality known to one of skill in the art. The methods of the disclosed subject matter are not limited to such images, and can be applied to images of any dimension, e.g., a two-dimensional picture, a three-dimensional volume, or a four-dimensional space. For a two-dimensional image or a three-dimensional image, the domain of the image is typically a two-dimensional rectangular array or a three-dimensional rectangular array, where each pixel or voxel can be addressed with reference to a set of two or three mutually orthogonal axes.

Figure 3A:
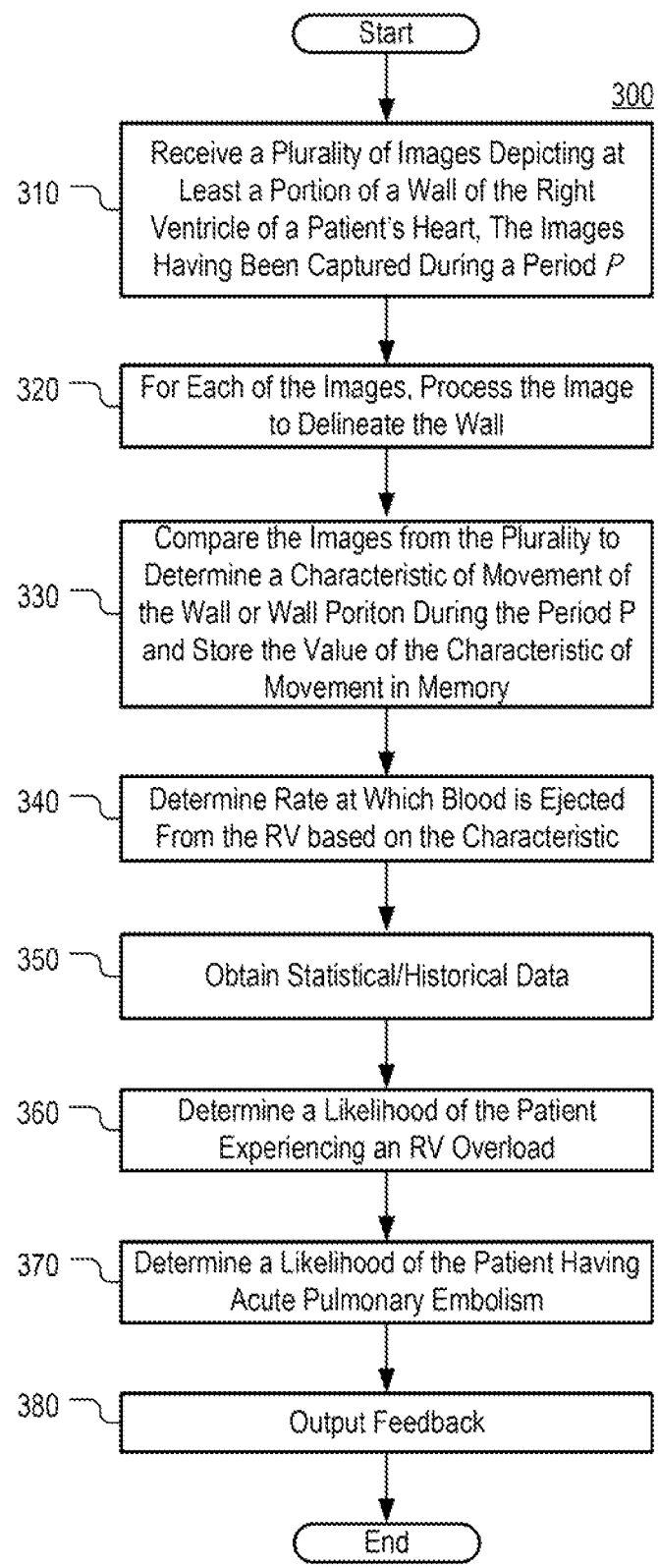
FIG. 3A is an example of a flow diagram of a process for monitoring the condition of a patient's heart in accordance with some embodiments of the disclosed subject matter.

FIG. 3A depicts an example of a flowchart of a process 300 in accordance with some embodiments of the disclosure. In some embodiments, process 300 may obtain images of heart 100 of patient 210, detect abnormalities in the operation of the heart based on the images, and alert medical personnel to the abnormality. By extracting information from the images of the patient's heart, process 300 may thus aid medical personnel in diagnosing APE, or RV overload, in the early stages of its development.

Figure 3B:
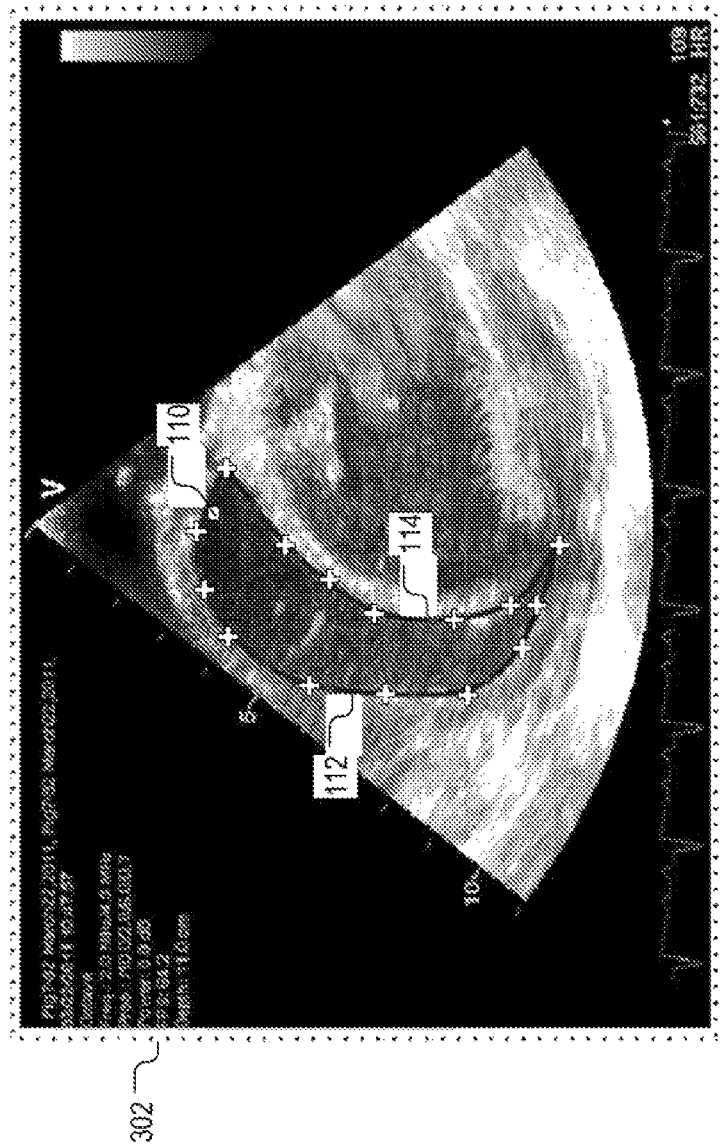
FIG. 3B is an example of an echocardiogram of a patient's heart in accordance with some embodiments of the disclosed subject matter.

At 310, a plurality of images that depict at least a portion of a wall of the right ventricle of a patient's heart are received. Each of the images may be captured by an image capturing device, such as the device 220, during a period P. The period P may encompass a portion of the cardiac cycle, a single cardiac cycle, or a plurality of cardiac cycles. For example, the images can be echocardiogram images, such as image 302 of heart 100, which is shown in FIG. 3B, in some embodiments.

At 320, one or more of the images in the plurality are processed to determine at least one of the shape and the location of the wall or wall portion of RV 110 that is depicted in each of the images. More precisely, in some embodiments, the wall may be delineated automatically by using image processing techniques (e.g., edge detection or pattern recognition). Additionally or alternatively, in some embodiments, the wall may be delineated semi-automatically by having a user, such as radiologist, manually place a set of boundary points on each of the images, and by passing a spline across the boundary points in each set afterwards. An example of a set of boundary points with a spline passed across is depicted in FIG. 3B. Although in the example of FIG. 3B both walls of RV 110 are delineated, in some embodiments only one of the walls, or a portion of that wall, may be delineated.

At 330, images in the plurality are compared to determine the value of at least one characteristic of movement of at least a portion of a wall of the right ventricle. The characteristic of movement may be any metric that is based on at least one of (a) the shape of the wall, or wall portion, in a first image and the shape of the wall, or wall portion, in a second image and (b) the location of the wall, or wall portion, in the first image and the location of the wall, or wall portion, in the second image. In some embodiments, the characteristic of movement may be determined by comparing at least one of the shape and the location of the wall, or wall portion, in different images from the plurality. In that regard, in some embodiments, the characteristic of movement may be a metric that describes the manner in which the wall, or wall portion, moves as heart 100 contracts and relaxes.

In some embodiments, the characteristic of movement may be a binary value indicating whether or not RV 110 is exhibiting a particular pattern of movement, such as a waving septal motion, or unstable septal motion. Furthermore, in some embodiments, the characteristic of movement may be a non-binary value that indicates the extent to which a particular pattern of movement, or lack thereof, is exhibited. Examples of image processing techniques are provided in the discussions with respect to FIGS. 4A-8B. Examples of characteristics of movement that may be determined at 330 include:

C1: Manifestation of waving septal motion;
C2: Frequency, amplitude, or another property of the waving septal motion;
C3: Change (increase/decrease) of curvature of the septum;
C4: An amount by which the curvature has changed;
C5: Speed at which a wall of RV 110 moves;
C5: Distance by which a wall (or a point on the wall) of RV 110 moves;
C6: Change in the area of the right ventricle, as a result of the heart contracting;
C7: Change in the shape of RV 110, or at least a portion of a wall of RV 110;
C8: Similarity in the movements of different walls of RV 110;
C9: Correlation between the movements of different walls of RV 110;
C10: Stability of the movements of RV 110;
C11: Deviation in displacement of septum 114 during the cardiac cycle;
C12: One of variance, average value, median value, or another statistical property of one of displacement, speed, acceleration, shape, or curvature of a wall (or portion thereof) of RV 110; and
C13: Correlation between displacement, speed, acceleration, shape, or curvature, or another property of two walls of RV 110 (e.g., walls 112 and 114).

Figure 3C:
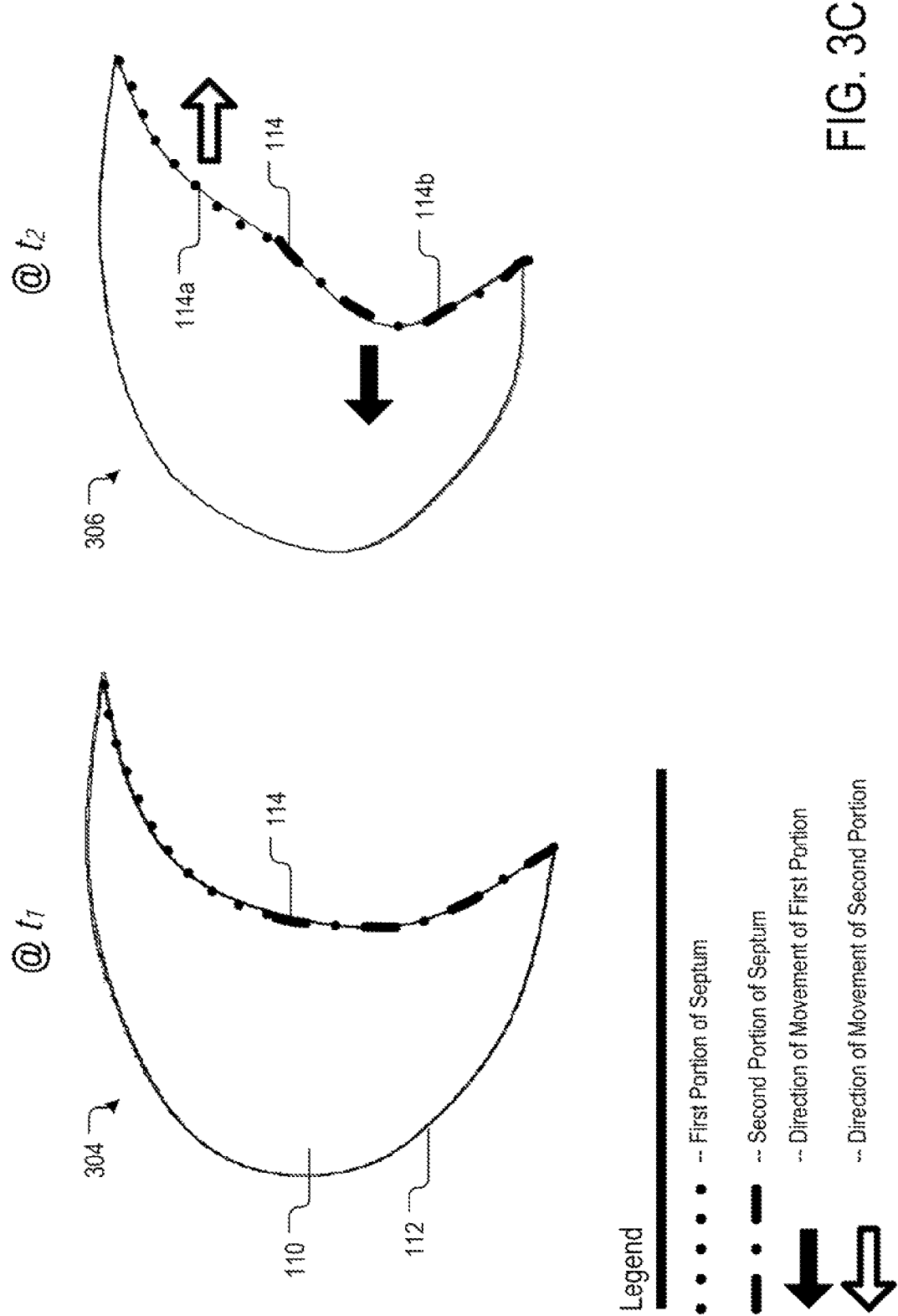
FIG. 3C is an example diagram of a right ventricle of a heart at different time instants during the heart's operation in accordance with some embodiments of the disclosed subject matter.

In some embodiments, at 330, a determination may be made of whether septum 114 is moving in a wavelike pattern as heart 100 contracts and relaxes. The determination may be based on at least a first image and a second image from the plurality of images obtained at 310. FIG. 3C depicts an example of a wavelike pattern of movement. In particular, FIG. 3C depicts images 304 and 306 of RV 110 that are taken at time instants $t_1$ and $t_2$, respectively. As illustrated, waving septal motion is manifested by portion 114a of septum 114 moving away from RV 110 and portion 114b of the septum moving towards RV 110. Experiments performed on pigs with induced APE have revealed that RV overload due to APE may result in the septum moving in the illustrated pattern. Thus, in some embodiments, at 330, image processing techniques may be employed to detect waving septal motion and collect information about it when it occurs.

In some embodiments, at 330, a determination may be made of whether the curvature of septum 114 changes abnormally as heart 100 contracts and relaxes. The determination may be based on at least a first image and a second image from the plurality obtained at 310. Making the determination is desirable because experiments performed on pigs with induced APE have revealed that RV overload due to APE may change the curvature of the septum considerably. Accordingly, in some embodiments, image processing techniques may be employed to detect when the curvature of septum 114 changes abnormally. Thus, in some embodiments, at 330, image processing techniques may be employed to gather information about the curvature of septum 114 and determine whether it changes abnormally.

In some embodiments, at 330, the movements of walls 112 and 114 may be compared and a determination may be rendered as to how similar the movements are. The determination may be made based on at least the first image and the second image from the plurality obtained at 310. For example, in some embodiments, the determination may be based on one set of the first image and second image. Making the determination is desirable because experiments performed on pigs with induced APE have revealed that during RV overload the movements of septum 114 become more independent from the movements of free outer wall 112. In that regard, in some embodiments, image processing techniques may be utilized to monitor the movements of walls 112 and 114 and measure how synchronous the movements of walls 112 and 114 are.

In some embodiments, at 330, the speed and/or the extent to which RV 110 contracts may be determined. The determination may be based on at least the first image and the second image from the plurality obtained at 310. For example, in some embodiments, the determination may be based on one set of the first image and second image. Changes in the volume of RV 110 that occur as heart 100 contracts may indicate the speed at which blood is ejected from RV 110. Experiments performed on pigs with induced APE have revealed that blood circulation becomes slower during RV overload. Accordingly, in some embodiments, at 330, the first image and the second image may be processed to detect changes in the visible area of RV 110 in the plurality of images and the rate at which those changes occur. The area, in some embodiments, may be the area of the cross-section of RV 110 that is visible on the images. In some embodiments, the area may be used as a surrogate for the right ventricle's volume. This information may in turn be further processed to determine the rate at which blood flows out of RV 110.

Figure 3D:
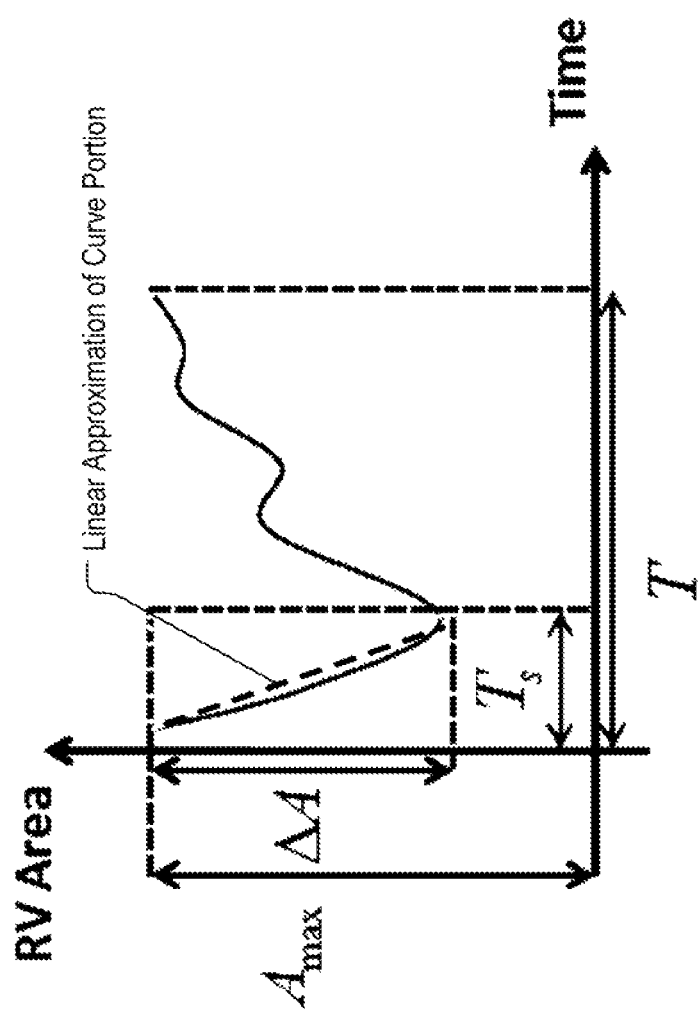
FIG. 3D is an example diagram of a signal representing the area of the right ventricle of the heart of FIG. 3C during the cardiac cycle.

At 340, the rate at which blood is ejected from the RV 110 is determined based on characteristics of movement determined at 330. In some embodiments, the rate may be determined based on the maximum change in the area of RV 110 during a given cardiac cycle and the speed at which the rate changes. The change in the area and the speed may be determined by comparing the delineations of RV 110 in images that were taken during the same cardiac cycle. Computing the area of RV 110 over an entire cardiac cycle may yield the 1-dimensional signal depicted in FIG. 3D. To estimate the speed at which blood is ejected by RV 110, the change of the RV area during the type of a systolic phase $T_S$ may be computed. As illustrated, RV 110 exhibits somewhat of an acceleration during the systolic phase, however the speed may be approximated as a linear function with respect to time as shown by the dashed line. With that said, in some embodiments, the rate at which blood is ejected by RV 110 may be represented as:

$$\lambda = \Delta A / T \quad \text{(Eq. 1)}$$

where $\lambda$ is the rate at which blood is ejected, $\Delta A$ is the change in the area during the time of the systolic phase $T_s$ of the cardiac cycle, and T is the duration of the cardiac cycle.

Furthermore, in some embodiments, the rate at which blood is ejected by RV 110 may be represented as:

$$\lambda = \left( \frac{\frac{\Delta A}{A_{max}}}{\frac{T}{T_s}} \right) \quad \text{(Eq. 2)}$$

where, $\lambda$ is the rate at which blood is ejected, $\Delta A$ is the change in the area during the time of the systolic phase $T_s$, $A_{max}$ is the maximum area of RV 110 reached at the end of the diastolic phase and the beginning of the systolic phase of the cardiac cycle, and T is duration of the cardiac cycle, and $T_s$ is the duration of the systolic phase of the cardiac cycle. In some aspects Equation 2 may be advantageous over Equation 1 because it accounts for variations in the heart's systolic phase that occur naturally. The denominator accounts for this phenomenon by measuring the ratio of the heart cycle's duration and the systolic phase's duration. Furthermore, in some aspects, Equation 2 may be advantageous over Equation 1 because its nominator accounts for the percentage of blood volume being ejected from the heart's right ventricle, rather than the absolute volume. In some aspects, percentage of blood volume may be a better indicator of a heart's health as, in general, patients' hearts may vary in size.

At 350, historical or statistical data regarding the incidence of the characteristic of movement among healthy and/or unhealthy populations is determined. In some embodiments, the historical data may be obtained from experiments conducted on animals, such as pigs. For example, successive injections of about 30 um microspheres of Sephadex G50, manufactured by Pharmacia Fine Chemicals of Uppsala, Sweden, may be applied into the femoral veins of the pigs to induce APE. Afterwards, the incidence of different characteristics of movement of at least a portion of a wall of the pigs' right ventricles may be observed and recorded. Furthermore, the incidence of different characteristics of movement of at least a portion of a wall of the right ventricle in pigs who are known to be healthy may be observed and recorded. In this manner, information about the incidence of different characteristics of movement, and values thereof, for both healthy and unhealthy test animals may be collected.

In some embodiments, historical or statistical data regarding the incidence of the characteristic of movement in human patients may be obtained. For example, characteristics of movements of at least a portion of a wall the right ventricle of human subjects who are known to be healthy may be observed and recorded. As another example, characteristics of movements of at least a portion of a wall the right ventricle of human subjects who are known to be experiencing APE may be observed and recorded. In some embodiments, the historical data may be collected by system 200, or another system executing process 300. Specifically, the system may record the characteristics of movement of at least a portion of a wall of the right ventricle of patients that are being examined using the system, or their blood flow rate, and then the system may record diagnoses for those patients that are made by medical personnel. The diagnoses may be manually entered into the system by the medical personnel by using a keyboard or another suitable input device. In some embodiments, each diagnosis may classify each patient as healthy, experiencing APE, experiencing RV overload, or experiencing both APE and RV overload. In this manner, information about the incidence of different characteristics of movement, and values thereof, among both healthy and unhealthy populations of patients may be collected. Although, in the above examples, statistical/historical data regarding the incidence of different values of a characteristic of movement of at least a portion of a heart's wall among different types of test subjects is collected, in other examples, statistical/historical data may be collected that describes the incidence of different values for blood flow rate for the different types of patients.

At 360, a likelihood of patient 210 experiencing RV overload is determined. The likelihood of RV 110 being overloaded may be estimated by comparing the value of a characteristic of movement obtained at 330, or blood flow rate obtained at 340, to at least a portion of the statistical data obtained at 350. As discussed, the statistical data may define the incidence of different values for the characteristic of movement among at least one of healthy patients and/or patients who have been found to experience RV overload. Accordingly, this data may be used as a basis for calculating a likelihood of patient 210 experiencing RV overload. In some embodiment, the likelihood of a patient experiencing RV overload may be considered to be high if the value for the characteristic of movement obtained at 330 differs by three standard deviations from the mean for healthy patients. Additionally or alternatively, in some embodiments, the Bayes theorem may be used to perform the calculation. Furthermore, in some embodiments, where multiple characteristics of movement are determined at 330, a more complex probabilistic model may be used to estimate the likelihood of the patient experiencing RV overload. In that regard, the disclosure is not limited to any specific method for calculating the likelihood of patient 210 experiencing RV overload given a value of a characteristic of movement for that patient and a data set that describes the incidence of the characteristic of movement, or its value, among at least one of healthy patients and patients who were found to be experiencing RV overload.

At 370, a likelihood of patient 210 suffering from APE is determined. The likelihood may be estimated by comparing the value of characteristic of movement obtained at 330 to at least a portion of the statistical data obtained at 350. As discussed, the statistical data may define the incidence of a given value for the characteristic of movement among at least one of healthy patients and/or patients who have been found to have APE and it may be used as a basis for calculating a likelihood of patient 210 having APE. In some embodiments, the Bayes theorem may be used to perform the calculation. Furthermore, in some embodiments, where multiple characteristics of movement are determined at 330, a more complex probabilistic model may be used to estimate the likelihood of the patient experiencing RV overload. In that regard, the disclosure is not limited to any specific method for calculating the likelihood of patient 210 having APE given a value of a characteristic of movement for that patient and a data set that describes the incidence of the characteristic of movement, or its value, among at least one of healthy patients and patients who were found to have APE.

At 380, an indication of the characteristic of movement determined at 330 is output. The indication may be any number, alphanumerical string, sound, image, tactile feedback, or another suitable type of feedback, that is based at least partially on the value of the characteristic of movement of at least a portion of a wall of RV 110 that is determined at 330. In some embodiments, the indication may be the raw value of the characteristic that is stored in memory at 330. In some embodiments, the indication of the characteristic of movement may be an indication of whether patient 210 is experiencing RV overload, as determined at 360. In some embodiments, the indication of the characteristic of movement may be an indication of the likelihood of patient 210 having APE, as determined at 370. Outputting the indication of the characteristic of movement may include displaying any one of the above indications on a display screen (e.g., LCD monitor), playing a sound using an acoustic transducer (e.g., using text-to-voice conversion to speak the indications), generating tactile feedback, or transmitting any one of the above indications over a communications network to a remote processor-based device, such as a computer, for further use and/or processing. Furthermore, in some embodiments, where the likelihood of the patient having RV overload or APE is output, additional information about the size and/or type of the data set obtained at 350 may be output in order to enable medical personnel to better judge the reliability of the estimate.

Figure 4A:
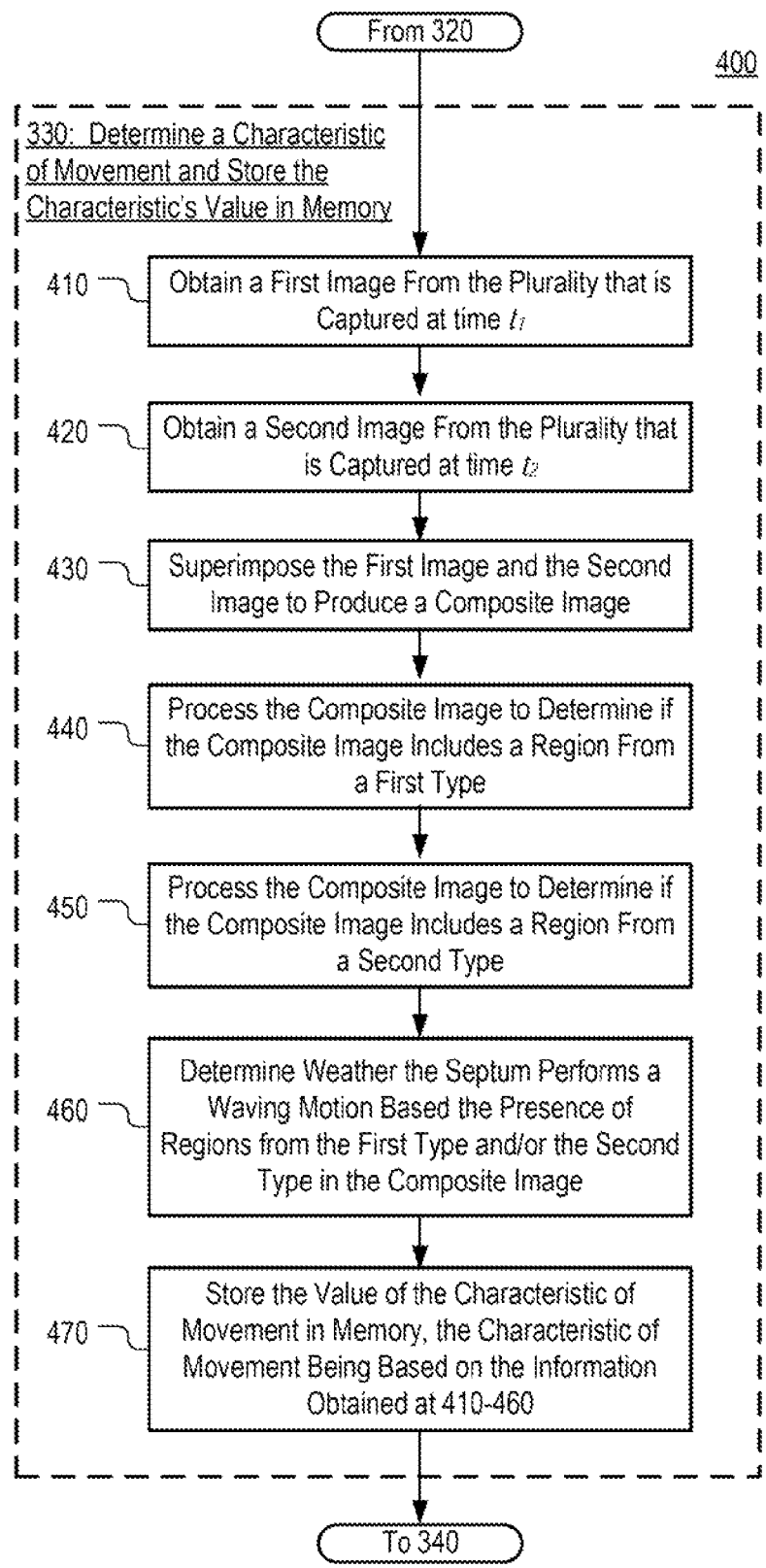
FIG. 4A is an example of a flow diagram of a process associated with detecting waving septal motion in accordance with some embodiments of the disclosed subject matter.
Figure 4B:
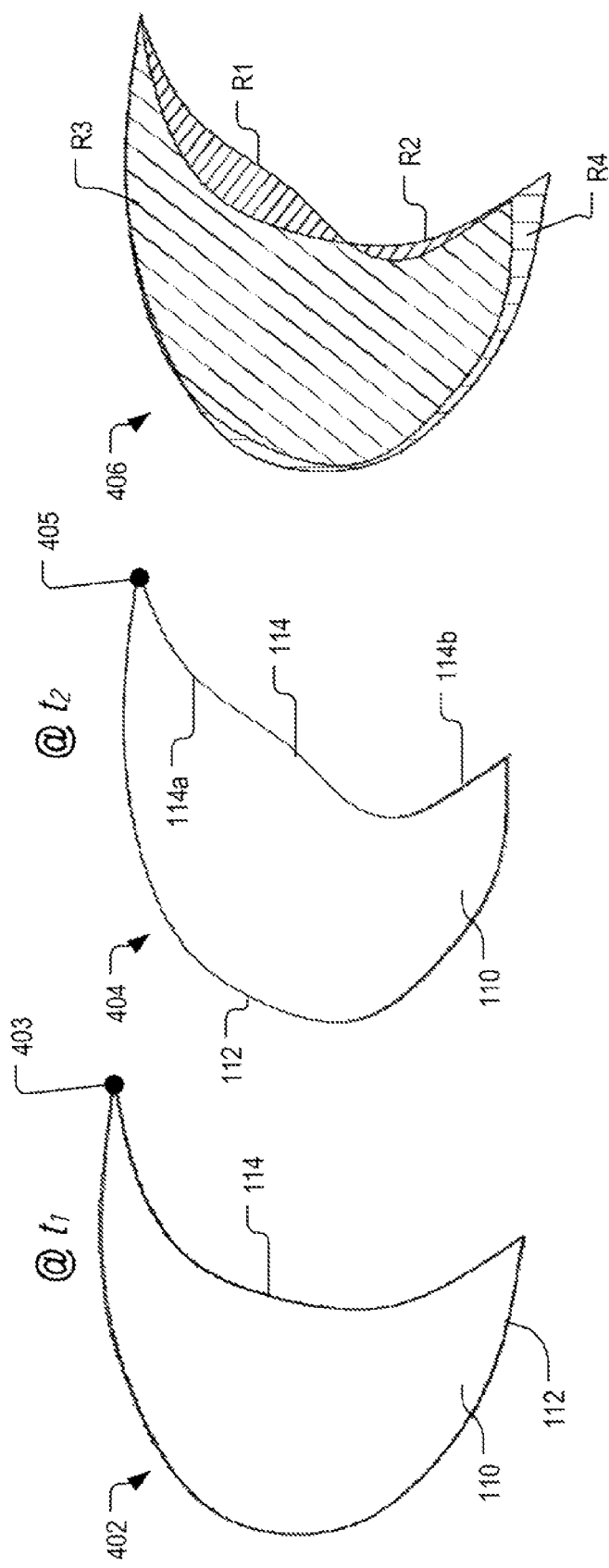
FIG. 4B is an example diagram of a heart's right ventricle during different time instants of the heart's operation in accordance with some embodiments of the disclosed subject matter.

FIG. 4A depicts an example of a flowchart of a process 400 for determining a characteristic of movement of at least a portion of a wall of RV 110, as specified at step 330 of process 300. In some embodiments, the characteristic of movement determined by process 400 may be based on a waving motion of septum 114. At 410, a first image from the plurality is selected. The first image may be captured approximately at the beginning of a cardiac cycle or at any other suitable point in time. At 420, a second image from the plurality is selected. The second image may be captured approximately in the middle of the same cardiac cycle or at any other suitable point in time. For example, the first image may be image 402 and the second image may be image 404. Both images are depicted in FIG. 4B.

At 430, the first image and the second image are superimposed to produce a composite image. An example of a composite image 406 is depicted in FIG. 4B. In some embodiments, superimposing the two images may include placing image 402 on top of image 404, such that anchor point 403 coincides with anchor point 405. As illustrated in FIG. 4B, composite image 406 includes regions R1-R4. Region R1 is defined by portion(s) of septum 114 and belongs to image 404 (second image), but not to image 402 (first image). Region R2 is also defined by portion(s) of septum 114, but belongs to image 402 (first image) and not to image 404 (second image). Region R3 belongs to both the first image and the second image. Region R4 belongs to image 402 (first image) only. As can be seen, Regions R1, R2, and R4 of composite image 406 are regions where images 402 and 404 do not overlap.

At 440, composite image 406 is processed to determine whether it includes at least one region from a first type. Regions from the first type may be regions defined at least partially by septum 114 that belong to a first one of the images used to create composite image 406 (e.g., image 402), but not to a second one of those images (e.g., image 404). At 450, composite image 406 is processed to determine whether it includes at least one region from a second type. Regions from the second type may be regions that are defined at least partially by septum 114 and belong to the second one of the images used to create composite image 406 (e.g., image 404), but not to the first one (e.g., image 402). An example of a region from the first type is Region R2 and an example of a region of the second type is Region R1. In some embodiments, the presence of the regions from each of the two types may be determined automatically, by using pixel clustering or another suitable technique.

At 460, a determination is made whether septum 114 performs a wave motion. In some embodiments, septum 114 may be found to perform a wave motion if at least one of a region from the first type or a region from the second type is present in composite image 406. In other embodiments, septum 114 may be considered to perform a wave motion if at least one region from the first type and at least one region from the second type are present in composite image 406. At 470, a value for the characteristic of movement is determined and stored in a memory (e.g., RAM, flash, network storage) of the system 200, of another system that is executing process 300, etc. The value may be based on any of the information determined at steps 410-460. In some embodiments, the value may be a binary value that indicates whether or not septum 114 performs a wave motion. In other embodiments, the stored value may be non-binary and may indicate one or more characteristics of the wave motion, such as size of Region R1 or Region R2, how far or close each region extends from wall 112 of RV 110, relative sizes of the regions, or any other suitable metric.

Figure 5A:
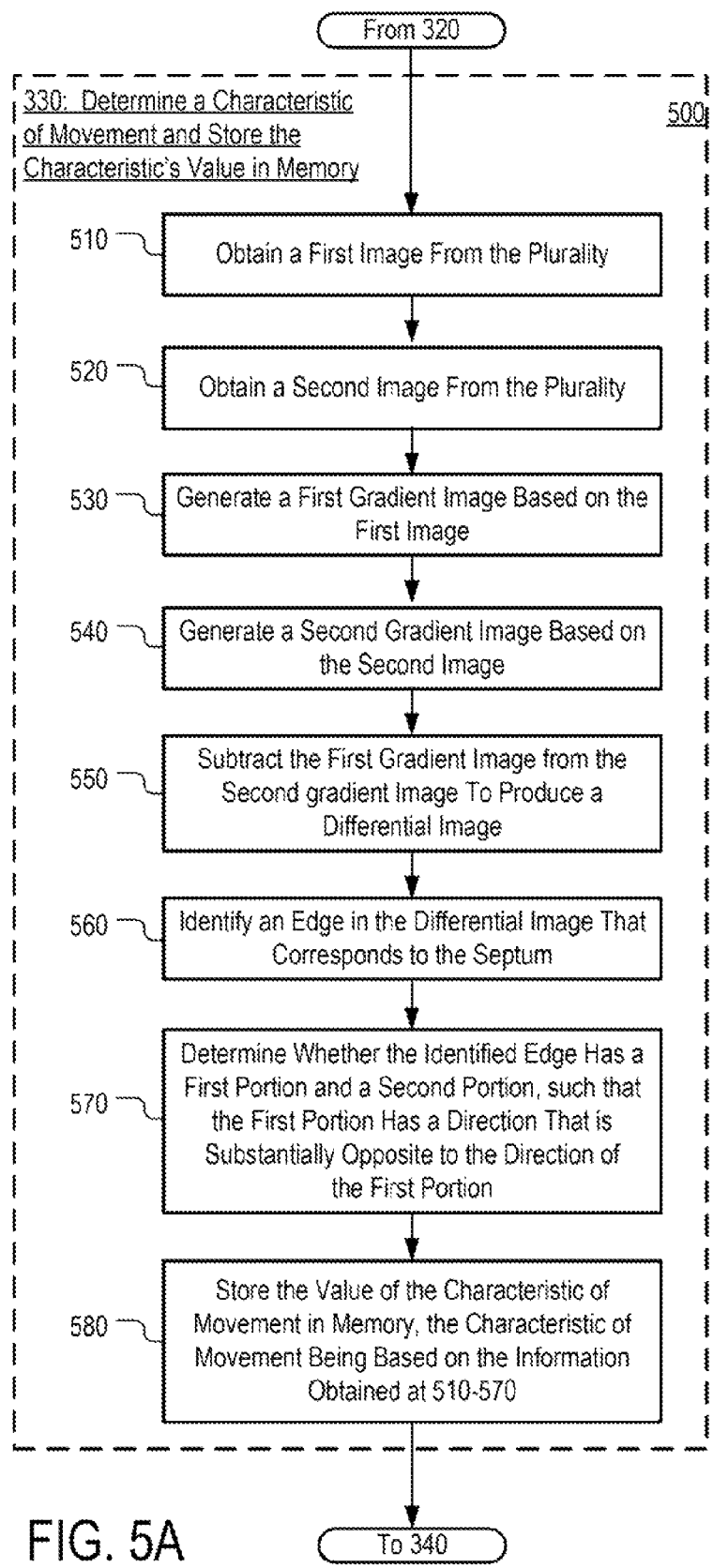
FIG. 5A is another example of a flow diagram of a process associated with detecting waving septal motion in accordance with some embodiments of the disclosed subject matter.

FIG. 5A depicts another example of a flowchart of a process 500 for determining a characteristic of movement of at least a portion of a wall of RV 110, as specified at step 330 of process 300. In some embodiments, the characteristic of movement determined by process 500 may also be based on a waving motion of septum 114. At 510, a first image from the plurality is selected. The first image may be captured approximately at the beginning of the cardiac cycle or any other suitable point in time. At 520, a second image from the plurality is selected. The second image may be captured approximately in the middle of the same cardiac cycle or any other suitable point in time. At 530, the first image is processed to obtain a first gradient image that is based on image intensity. The first gradient image includes an edge that corresponds to septum 114. At 540, the second image is processed to obtain a second gradient image that is also based on image intensity. The second gradient image also includes an edge that corresponds to septum 114.

Figure 5B:
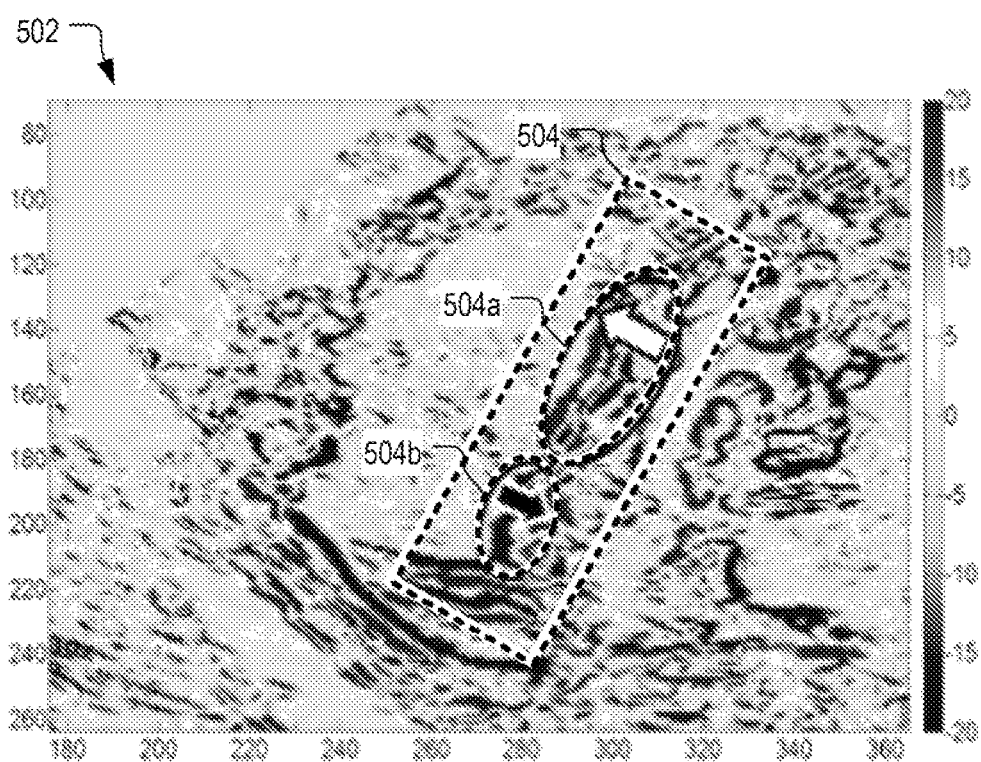
FIG. 5B is an example diagram of a composite gradient image of a heart in accordance with some embodiments of the disclosed subject matter.

At 550, the first gradient image is subtracted from the second gradient image to produce a differential image. An example of a differential image 502 is depicted in FIG. 5B. At 560, differential image 502 is processed to identify an edge that corresponds to septum 114. As discussed with respect to FIG. 3, the edge may be determined automatically and/or semi-automatically. For example, edge 504 may be identified. At 570, a determination is made whether edge 504 includes at least two portions that have approximately opposite gradient directions (e.g., portions 504a and 504b). By way of example, two portions of differential image 502 may be considered to have opposite gradient directions if the sums of pixel values in those portions have opposite signs. If such two portions are found to exist in the differential image, this may indicate that these portions have moved in opposite directions during the period starting when the first image was captured and ending with the capture of the second image. Accordingly, if such two portions exist, septum 114 may be considered to perform a wave motion.

At 580, a value for the characteristic of movement is determined and stored in a memory (e.g., RAM, flash, network storage) of the system 200, of another system that is executing process 300, etc. The value may be based on any of the information determined at steps 510-570. In some embodiments, the value may be a binary value that indicates whether or not septum 114 performs a wave motion. In other embodiments, the stored value may be non-binary and may indicate one or more characteristics of the wave motion, such as the gradient direction(s) of at least one of portion 504a and portion 504b, an angle between the gradient directions of portion 504a and portion 504b, the sum/difference of the gradient directions of portion 504a and portion 504b, and/or any other suitable metric.

Figure 6A:
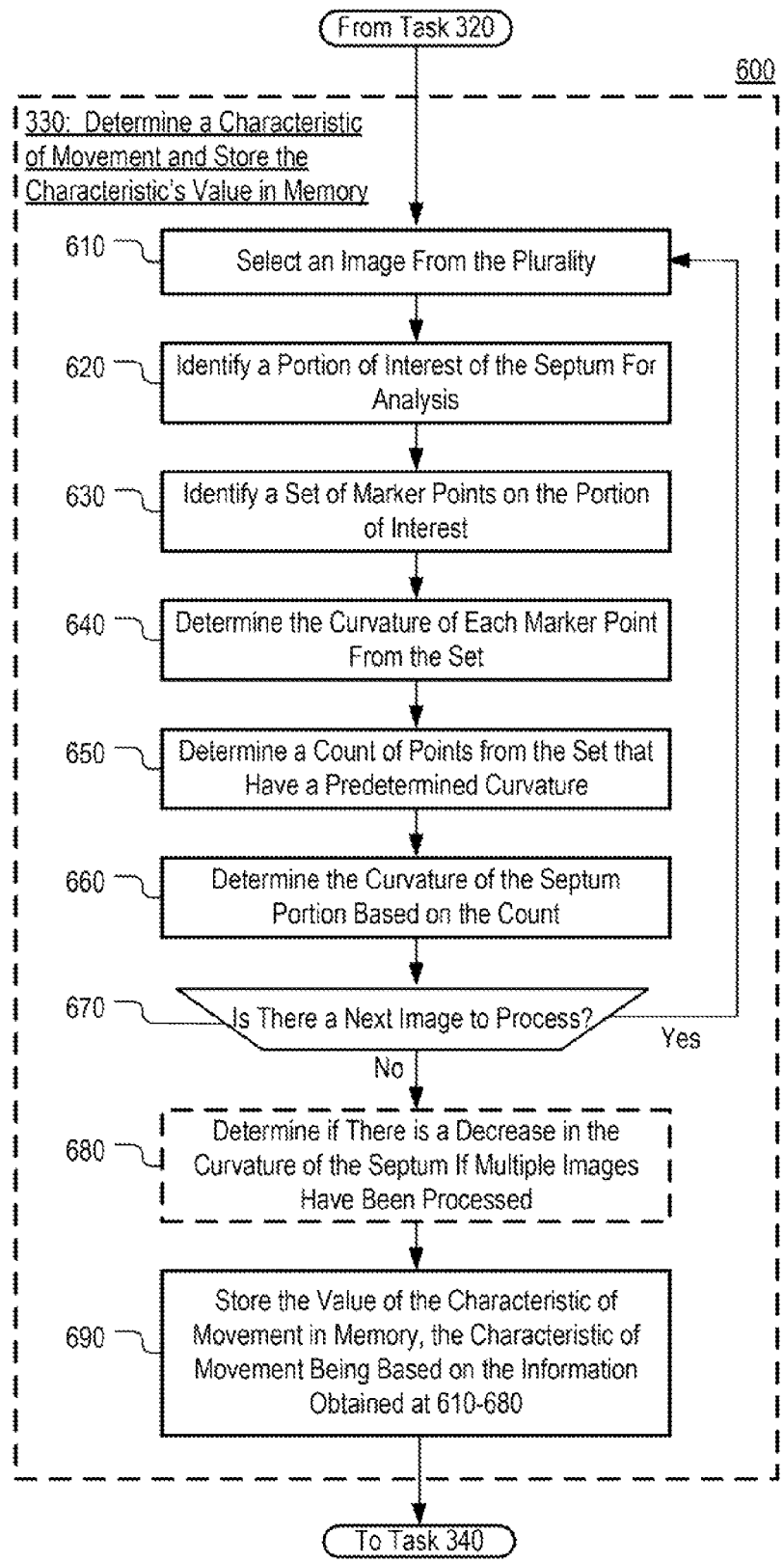
FIG. 6A is an example of a flow diagram of a process associated with detecting the curvature of at least a portion of a septum of a heart in accordance with some embodiments of the disclosed subject matter.
Figure 6B:
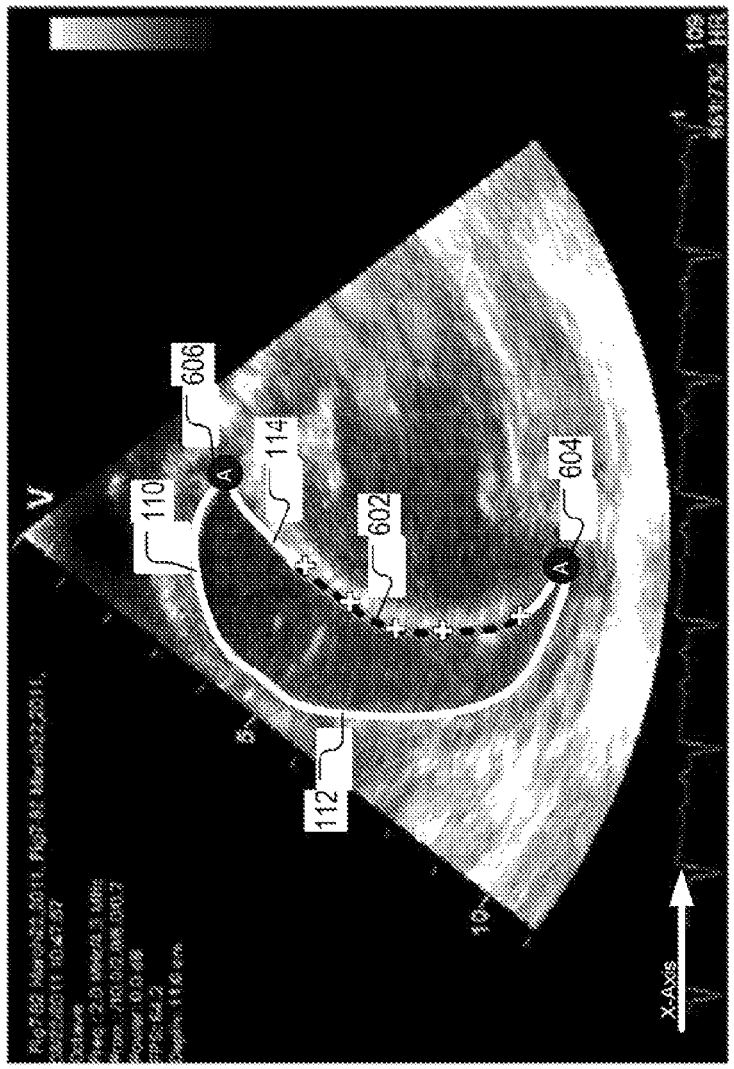
FIG. 6B is an example of an echocardiogram of a heart with the right ventricle delineated in accordance with some embodiments of the disclosed subject matter.

FIG. 6A depicts yet another example of a flowchart of a process 600 for determining a characteristic of movement of at least a portion of a wall of RV 110, as specified at step 330 of process 300. In some embodiments, the characteristic of movement determined by process 600 may be based on the curvature of septum 114. At 610, an image from the plurality is selected. At 620, a portion of interest of septum 114 is identified. In some embodiments, the portion of interest may include the whole of septum 114, and in other embodiments the portion of interest portion may include only a portion of septum 114, such as middle portion 602. As illustrated in FIG. 6B, middle portion 602 may include the middle three-fifths of septum 114, and the full length of septum 114 may span between anchor points 604 and 606. At 630, a set S of marker points is identified. The marker points in the set S may be situated along the portion of interest that is identified at 620. In some embodiments, the marker points in the set S may be spaced apart at equal distances from each other. Although, in this example, the set S includes 50 marker points, in other examples it can include any number of marker points.

At 640, the local curvature for each marker point P in the set S is determined. By way of example, the local curvature may be represented as:

$$\kappa = \left|\frac{d\phi}{ds}\right|$$

where, κ is the local curvature, ϕ is the inclination of the tangent to the portion of interest at the marker point P relative to an axis (e.g., the x-axis), and s is the length of middle portion 602.

At 650, a count of all marker points in the set S that have a predetermined curvature (e.g., either positive or negative) is taken. For example, the count of all points in the set S with positive curvature can be determined. At 660, the curvature of the septum, or a portion thereof of interest, is determined based on the count. By way of example, if the count of marker points with positive curvature exceeds the count of points with negative curvature, septum 114, or a portion thereof of interest, may be estimated to have positive curvature. As another example, if the count of marker points with positive curvature exceeds the count of points with negative curvature by a threshold amount, septum 114, or a portion thereof of interest, may be estimated to have positive curvature.

At 670, a determination is made of whether another image from the plurality needs to be processed. This determination can be made on any suitable basis. For example, this determination may be based on whether all images in a group of images (e.g., the plurality of images received at step 310 or a portion thereof) have been processed or based on a counter exceeding a threshold. If there is a next image to process, process 600 returns to 610 and steps 610-660 are executed for the new image. Otherwise, process 600 proceeds to 680.

At 680 and 690, a value for the characteristic of movement is determined and stored in a memory (e.g., RAM, flash, network storage) of the system 200, of another system that is executing process 300, etc. The value may be based on any of the information determined at steps 610-680. In some embodiments, the value may be a binary value that indicates whether the shape of septum 114 is abnormal. For example, the shape of septum 114, or portion thereof, may be considered abnormal if the count of marker points with a positive curvature exceeds the count of marker points with a negative curvature in the same image by a predetermined threshold amount (e.g., 20). In some embodiments, the value of the characteristic of movement may be a binary value indicating whether the shape of septum 114, or a portion thereof, has changed abnormally during a predetermined period. To determine whether the curvature of septum 114 decreased during a predetermined period, the count of marker points with positive curvature in a first image taken at the beginning of the period may be compared to the count of points with positive curvature in a second image that is taken at the end of the period. For example, if the count of marker points with positive local curvature in the first image is greater than the count of marker points with positive curvature in the second image, by a predetermined threshold (e.g., 20), the curvature of septum 114 may be estimated to have changed abnormally. Furthermore, in some embodiments, the value of the characteristic may be a non-binary value. For example, the value of the characteristic may be based on: the difference between the count of marker point(s) with a positive curvature and the count of the marker point(s) with a negative curvature that are found in the same image; the difference between the counts of marker points with a positive curvature that are found in different images; the difference between the counts of marker points with negative curvature that are found in different images; the count of marker points with a positive curvature that are found in a given image; the count of marker points with a negative curvature that are found in a given image; or any other suitable metric.

Figure 7A:
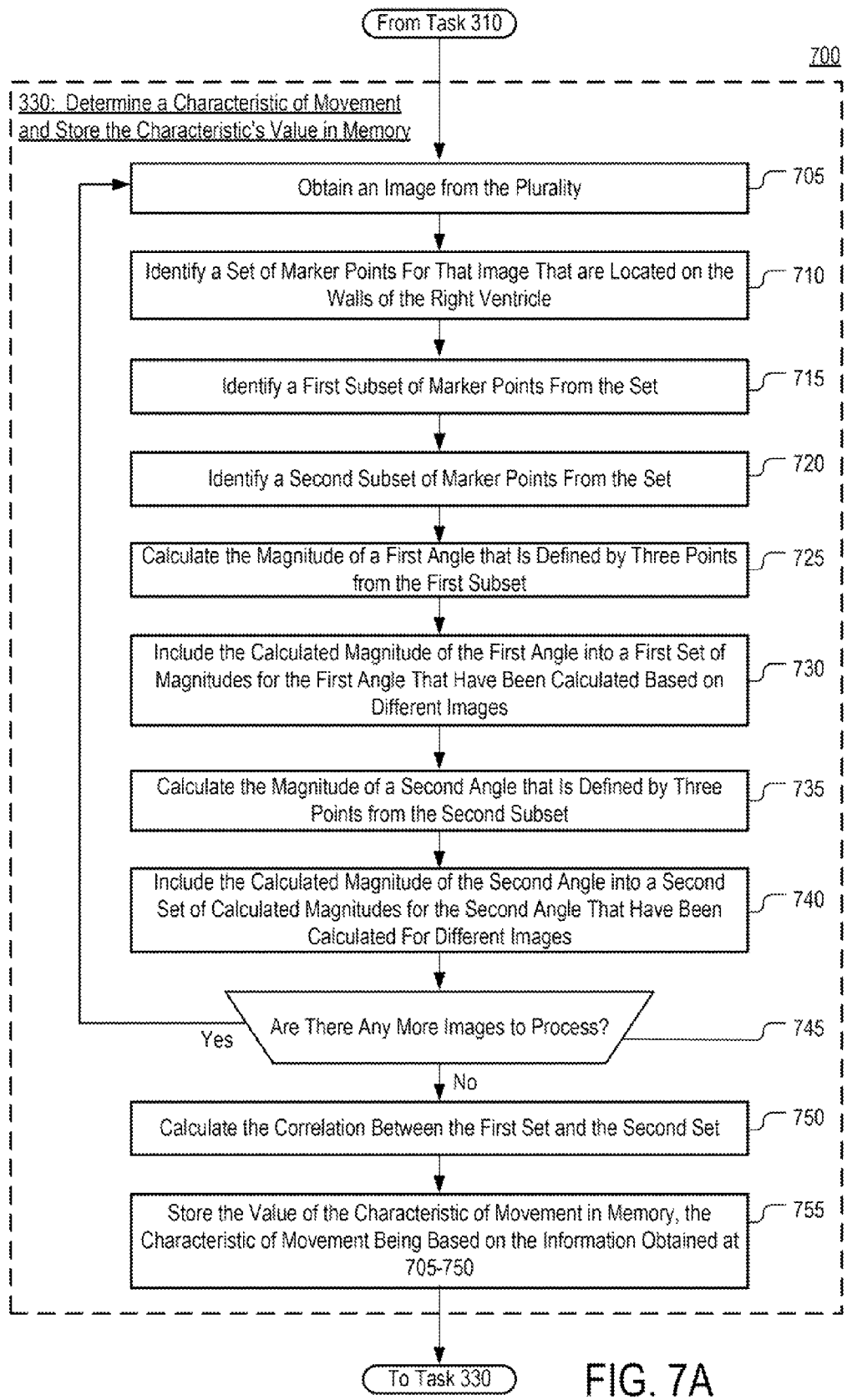
FIG. 7A is an example of a flow diagram of a process associated with detecting correspondence between the movements of different walls of the right ventricle of a patients' heart in accordance with some embodiments of the disclosed subject matter.
Figure 7C:
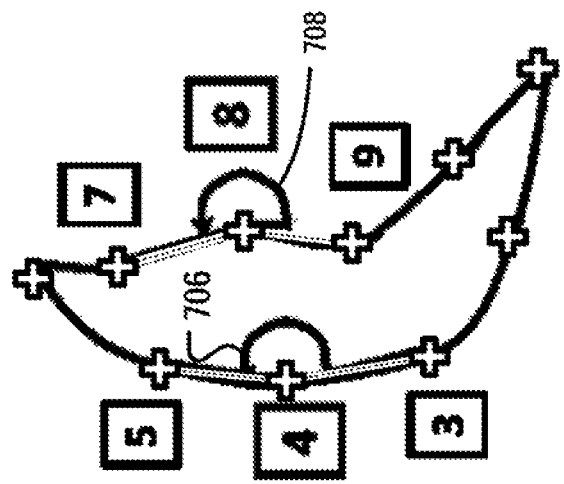
FIG. 7C is an example of a diagram of a right ventricle of a human heart in accordance with some embodiments of the disclosed subject matter.
Figure 7B:
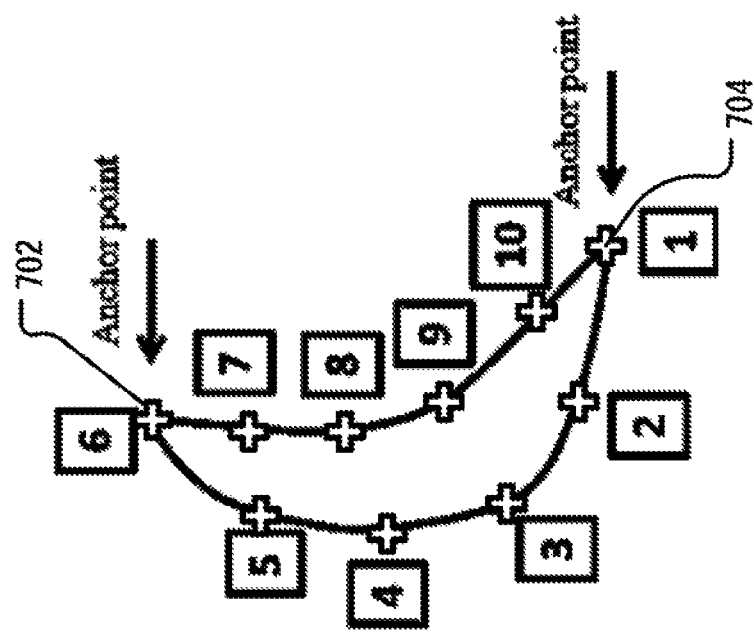
FIG. 7B is an example of a diagram of a right ventricle of a human heart in accordance with some embodiments of the disclosed subject matter.

FIG. 7A depicts still another example of a flowchart of a process 700 for determining a characteristic of movement of at least a portion of a wall of RV 110, as specified at step 330 of process 300. In some embodiments, the characteristic of movement determined by process 700 may be based on the correlation between the movements of different walls, or portions thereof, of RV 110. At 705, an image from the plurality obtained at 310 is selected. An example of an obtained image is depicted in FIGS. 7B-C. At 710, a set Q of marker points that are situated on the walls of RV 110 is identified. In some embodiments, an initial set of 100 (or any other suitable number) marker points for the image may be identified. The points in the initial set may be situated on the walls of RV 110 and may be equally spaced from one another. Afterwards, 10 (or any other suitable number) points from that set may be selected for inclusion in the set Q, such that Points 1 and 6 are situated at anchor points 702 and 704, as illustrated in FIG. 7B, Points 2-5 are situated on wall 112 of RV 110, and Points 7-10 are situated on septum 114. At 715, a first subset of the set of marker points Q is selected, such that all marker points in the first subset set lie on wall 112. In this example, the first subset includes Points 3-5. At 720, a second subset of the set of marker points Q is selected, such that all marker points in the second subset lie on septum 114. In this example, the first subset includes Points 7-9.

At 725, the magnitude of a first angle that is defined by the marker points in the first subset is calculated. For example, the first angle may be angle 706 shown in FIG. 7C. As illustrated, the arms of angle 706 may lie on marker points (Points 3 and 5) that are located on different sides of a third marker point (Point 4) from the first subset that is coincident with the vertex of the first angle. At 730, the calculated magnitude of the first angle is included in a first set of magnitudes for the first angle. Each magnitude in the first set of magnitudes is calculated based on a different image from the plurality in the manner discussed with respect to steps 705-725.

At 735, the magnitude of a second angle that is defined by the marker points in the second subset is calculated. For example, the second angle may be angle 708 shown in FIG. 7C. As illustrated, the arms of angle 708 may lie on marker points from the second subset (Points 7 and 9) that are located on both sides of a third marker point from the second subset (Point 8) that is coincident with the vertex of the second angle. At 740, the calculated magnitude of the second angle is included in a second set of magnitudes for the second angle. Each magnitude in the second set of magnitudes is calculated based on a different image from the plurality in the manner discussed with respect to steps 705-735.

At 745, a determination is made whether there is a next image to process. This determination can be made on any suitable basis. For example, this determination may be based on whether all images in a group of images (e.g., the plurality of images received at step 310 or a portion thereof) have been processed or based on a counter exceeding a threshold. If there is a next image to process, steps 705-745 are repeated for the next image. Otherwise, the execution of process 700 proceeds to 750. At 750, the correlation between the first set of magnitudes for the first angle (e.g., angle 706) and the second set of magnitudes for the second angle (e.g., angle 708) is determined. The correlation may indicate the degree to which the wall 112 and septum 114 move in synch with each other. Furthermore, the magnitudes of angles 706 and 708 that are measured for each individual image from the plurality may indicate the shape of walls 112 and 114 in that image.

At 755, a value for the characteristic of movement is determined and stored in a memory (e.g., RAM, flash, network storage) of system 200, of another system that is executing process 300, etc. The value may be based on any of the information determined at steps 705-750. In some embodiments, the value may be a binary value that indicates whether the movements of wall 112 and septum 114 are sufficiently correlated with one another. For example, if the correlation determined at 750 falls below a predetermined threshold, the movements of wall 112 and septum 114 may be considered insufficiently correlated, or out of synch. Furthermore, in some embodiments, the value of the characteristic of movement may be a non-binary value that is based on at least one of: the correlation determined at 350; one or more angle measurements from the first set; one or more angle measurements from the second set; and/or any other suitable metric that indicates the extent to which the movements of wall 112 and septum 114 are synchronous.

Figure 8A:
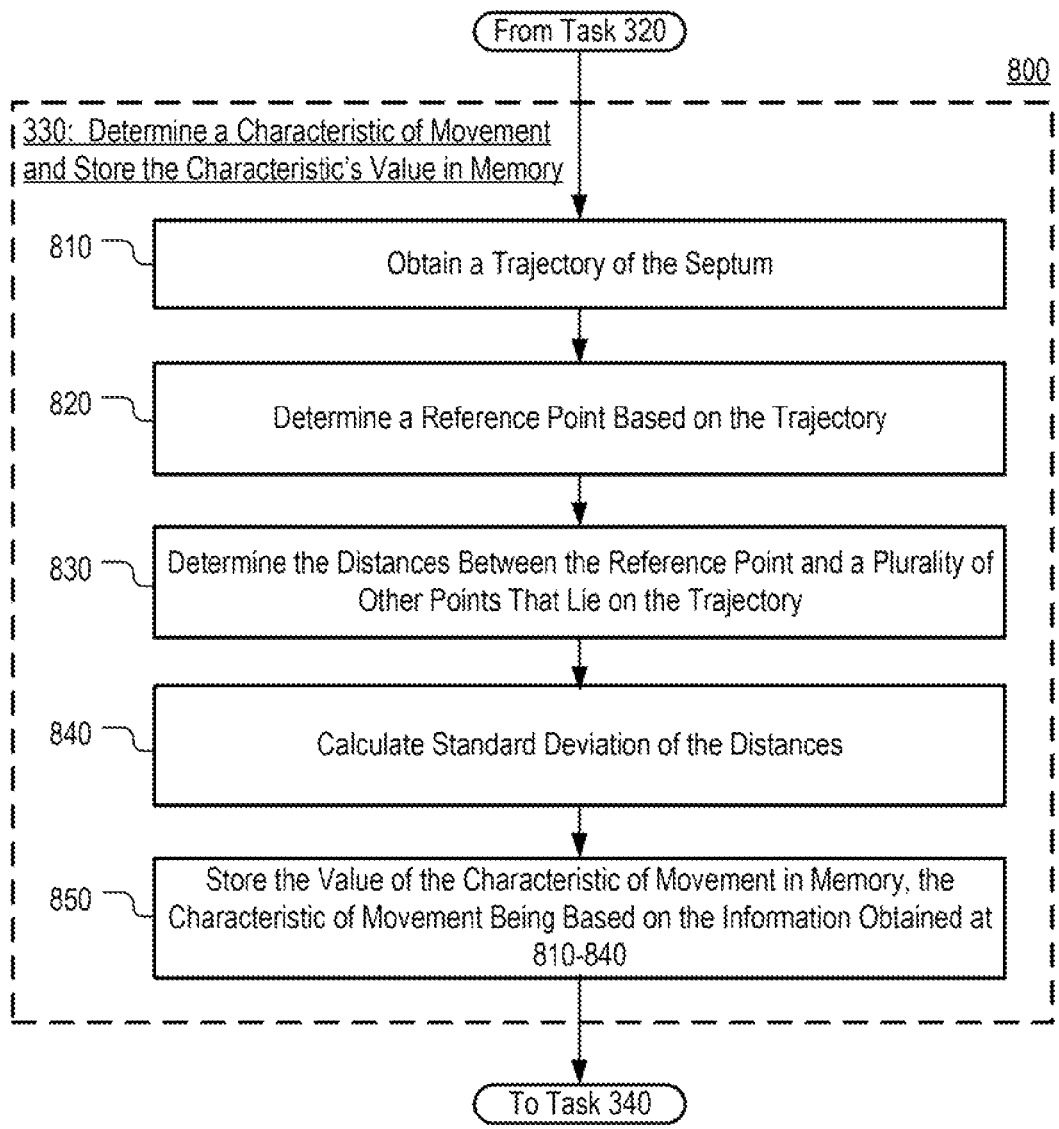
FIG. 8A is an example of a flow diagram of a process associated with detecting instability of the movements of a septum of a heart in accordance with some embodiments of the disclosed subject matter.
Figure 8B:
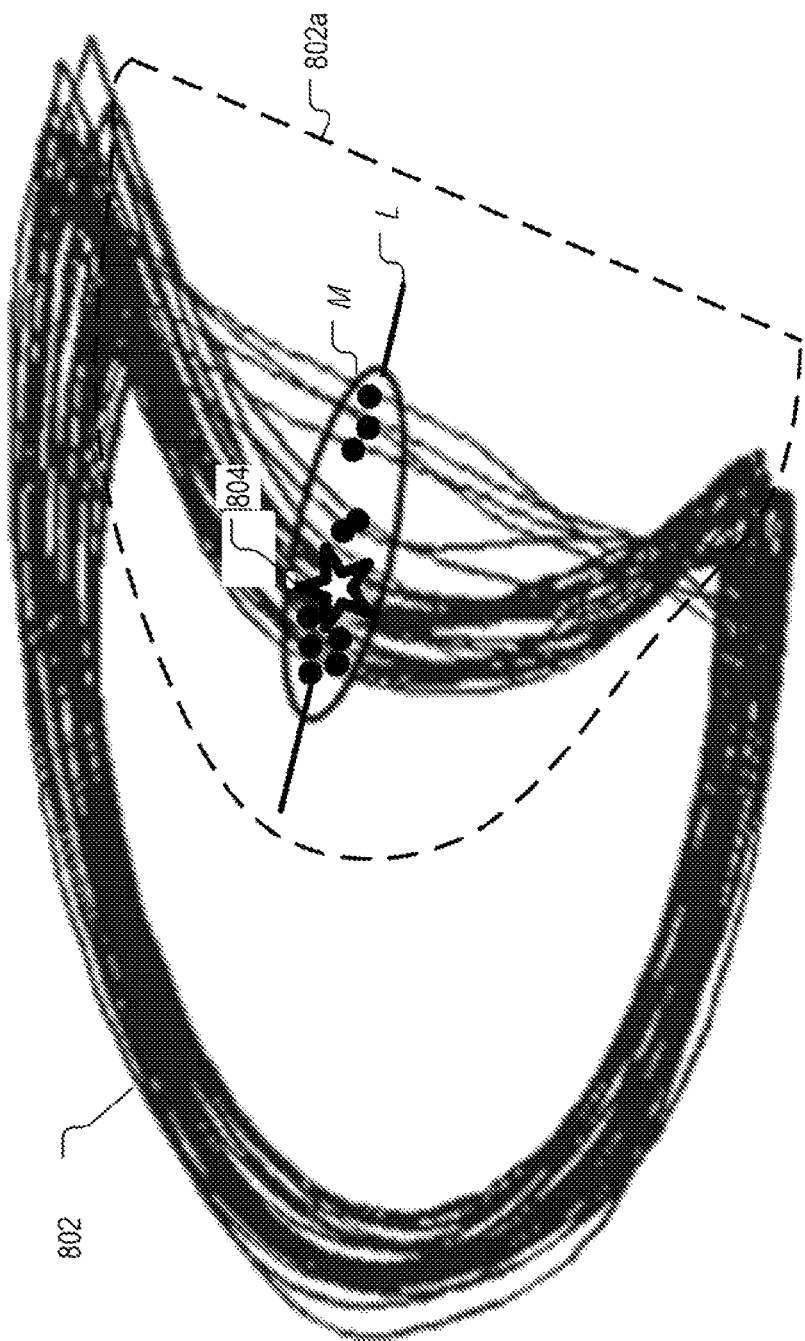
FIG. 8B is an example diagram of the trajectory of a heart's septum during the heart's operation in accordance with some embodiments of the disclosed subject matter.

FIG. 8A depicts still another example of a flowchart of a process 800 for determining a characteristic of movement of at least a portion of a wall of RV 110, as specified at step 330 of process 300. In some embodiments, the characteristic of movement determined by process 800 may be based on the variance in the movements of septum 114, or a portion thereof. At 810, the images from the plurality are processed to obtain a trajectory (such as trajectory 802 shown in FIG. 8B) of RV 110. As shown in FIG. 8B, trajectory 802 includes a portion 802a that represents the movements of septum 114. In some embodiments, the trajectory may be obtained by extracting the delineation of septum 114 from each image and superimposing it over the delineations of septum 114 from the other images in the plurality.

At 820, a reference point (such as reference point 804 of FIG. 8B) is selected. As illustrated in FIG. 8B, in some embodiments, the reference point may be selected by calculating the average of all points from portion 802a of trajectory 802 that lie on line L or all points from portion 802a of trajectory 802 that are located in region M. At 830, the distances between reference point 804 and a plurality of other points are calculated. In some embodiments, the plurality of other points may be composed entirely of points from portion 802a of trajectory 802 that lie on line L or, alternatively, points from region 802a that are located in the region M. At 840, the standard deviation of the set of distances obtained at step 830 is determined. At 850, a value for the characteristic of movement is determined and stored in a memory (e.g., RAM, flash, network storage) of system 200, of another system that is executing process 300, etc. The value may be based on any of the information determined at steps 810-840. In some embodiments, the value may be a binary value that indicates whether or not septum 114 moves in an unstable manner. In some embodiments, septum 114 may be considered to move in an unstable manner if the standard deviation exceeds a predetermined threshold. In some embodiments, septum 114 may be considered to move in an unstable manner if one of the distances calculated at 830 exceeds a predetermined threshold. In some embodiment, the stored value may be non-binary that indicates the extent to which the movements of septum 114 are stable, such as a value that is based on the standard deviation determined at 840.

Figure 9:
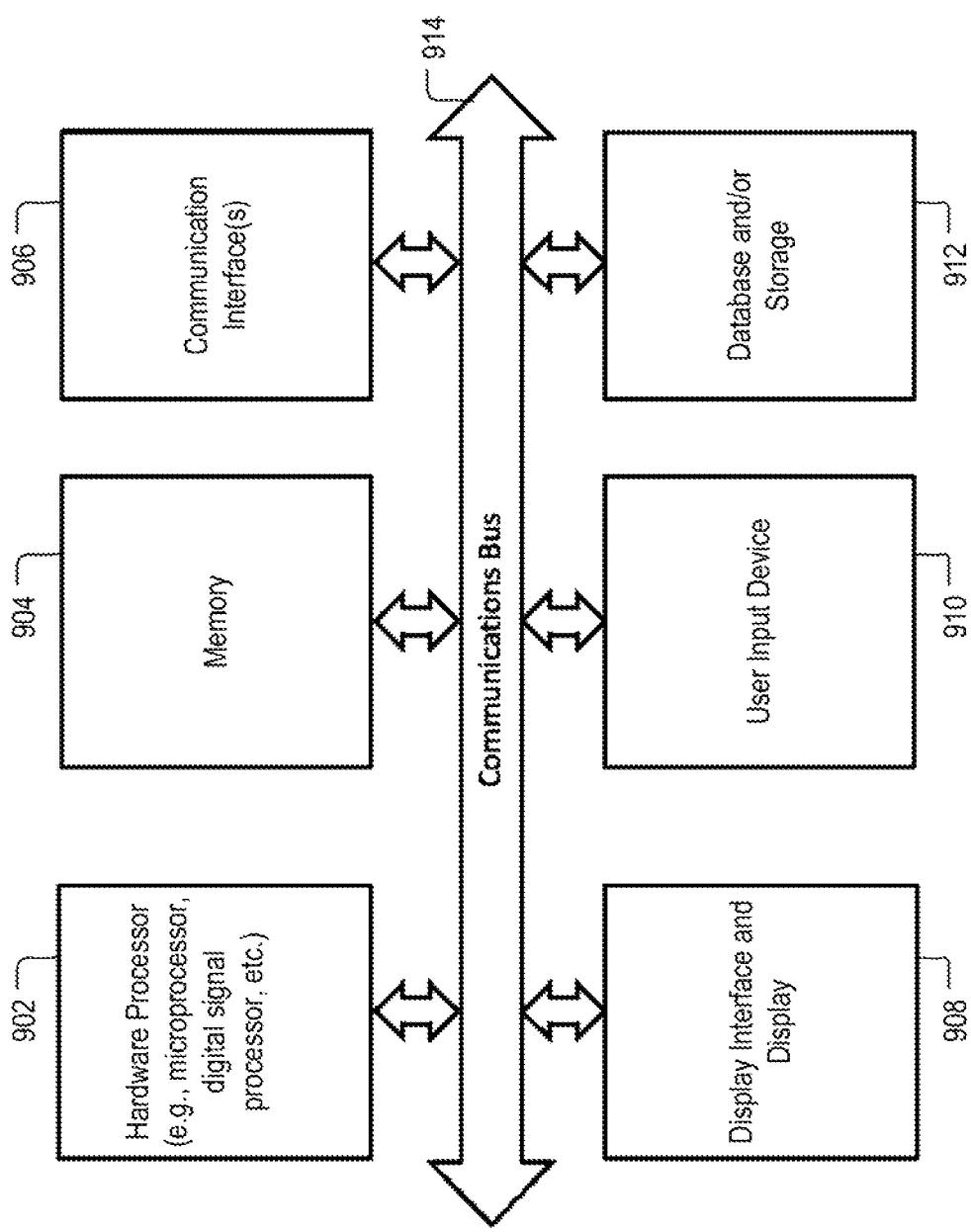
FIG. 9 is an example of a block diagram of hardware for a system for classifying images in accordance with some embodiments of the disclosed subject matter.

In accordance with some embodiments, any suitable hardware and/or software can be used to provide the mechanisms described herein (such as those illustrated in, and described in connection with, FIGS. 1-8B). For example, a general purpose device such as a computer or a special purpose device such as a client, a server, etc. can be used to execute software for performing the mechanisms described herein. Any of these general or special purpose devices, such as device 900 of FIG. 9, can include any suitable components such as a hardware processor 902 (which can be a microprocessor, digital signal processor, a controller, etc.), memory 904, communication interface(s) 906, a display interface and display 908, a user input device 910, a database and/or storage 912, a communications bus 914, etc. Communications interfaces 906 can enable the hardware and/or software to communicate with other communications networks (e.g., such as the Internet, wired networks, wireless networks, etc.), other equipment (e.g., such as medical scanning (e.g., such as a computed tomography scanner), diagnosis, display, etc. equipment), and/or any other suitable networks, devices, etc. This hardware and/or software can be implemented as part of other equipment (e.g., such as medical scanning (e.g., such as a computed tomography scanner), diagnosis, display, etc. equipment) or can be implemented as stand-alone equipment (which can be coupled to other equipment).

In some embodiments, any suitable computer readable media can be used for storing instructions for performing the processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

Furthermore, it should be noted that FIGS. 3-8B are provided as examples only. One or more of processes 300-800 may be performed by image processing device 230 (e.g., by a processor of image processing device 230), by device 900 (e.g., by processor 902), by any other suitable device, or by any suitable combination of devices, each device of which can include a suitable hardware processor. At least some of the steps in those processes may be performed in a different order than represented or performed concurrently. Furthermore, one or more of the steps in processes 300-800 may be altogether omitted.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims which follow. Features of the disclosed embodiments can be combined and rearranged in various ways.

What is claimed is:

1. A system for monitoring a condition of a patient's heart, the system comprising:
   a hardware processor that is configured to:
   receive a plurality of images of a first wall of the patient's heart, the plurality including a first image captured at a time $t_1$ and a second image captured at a time $t_2$;
   determine, based on the plurality of images, a first shape of at least a portion of the first wall at time $t_1$ and a second shape of the at least a portion of the first wall at time $t_2$, the first shape and the second shape being determined by using one or more image processing techniques;
   determine from at least the first shape and the second shape that the at least a portion of the first wall is moving in a wavelike pattern; and
   output an indication of an abnormality in the patient's heart in response to determining that the at least a portion of the first wall is moving in the wavelike pattern.

2. The system of claim 1, wherein the indication of the abnormality identifies a likelihood of the patient having pulmonary embolism.

3. The system of claim 1, wherein the indication of the abnormality identifies a likelihood of the patient experiencing a right ventricle (RV) overload.

4. A method for monitoring a condition of a patient's heart, the method comprising:
   receiving a plurality of images of a first wall of the patient's heart, the plurality including a first image captured at a time $t_1$ and a second image captured at a time $t_2$;
   determining, by a hardware processor, based on the plurality of images, a first shape of at least a portion of the first wall at time $t_1$ and a second shape of the at least a portion of the first wall at time $t_2$, the first shape and the second shape being determined by using one or more image processing techniques;
   determining from at least the first shape and the second shape that the at least a portion of the first wall is moving in a wavelike pattern; and
   outputting an indication of an abnormality in the patient's heart in response to determining that the at least a portion of the first wall is moving in the wavelike pattern.

5. The method of claim 4, wherein the indication of the abnormality identifies a likelihood of the patient having pulmonary embolism.

6. The method of claim 4, wherein the indication of the abnormality identifies a likelihood of the patient experiencing a right ventricle (RV) overload.

7. A non-transitory computer-readable medium containing computer-executable instructions that, when executed by a processor, cause the processor to perform a method for monitoring a condition of a patient's heart, the method comprising:
   receiving a plurality of images of a first wall of a patient's heart, the plurality including a first image captured at a time $t_1$ and a second image captured at a time $t_2$;
   determining, based on the plurality of images, a first shape of at least a portion of the first wall at time $t_1$ and a second shape of the at least a portion of the first wall at time $t_2$, the first shape and the second shape being determined by using one or more image processing techniques;

determining from at least the first shape and the second shape that the at least a portion of the first wall is moving in a wavelike pattern; and outputting an indication of an abnormality in the patient's heart in response to determining that the at least a portion of the first wall is moving in the wavelike pattern.

8. The non-transitory computer-readable medium of claim 7, wherein the indication of the abnormality identifies a likelihood of the patient having pulmonary embolism.

9. The non-transitory computer-readable medium of claim 7, wherein the indication of the abnormality identifies a likelihood of the patient experiencing a right ventricle (RV) overload.

\* \* \* \* \*